US012806313B2

(12) United States Patent
Pemberton et al.

(10) Patent No.: US 12,806,313 B2
(45) Date of Patent: Nov. 24, 2026

(54) LOW MOLECULAR WEIGHT HYDROGELS COMPRISING THIOGLYCOLIPIDS

(71) Applicant: ARIZONA BOARD OF REGENTS ON BEHALF OF THE UNIVERSITY OF ARIZONA, Tucson, AZ (US)

(72) Inventors: Jeanne E. Pemberton, Tucson, AZ (US); Laurel L Kegel, Tucson, AZ (US); Yu-Cheng Wang, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 659 days.

(21) Appl. No.: 18/551,535

(22) PCT Filed: Mar. 25, 2022

(86) PCT No.: PCT/US2022/021835
§ 371 (c)(1),
(2) Date: Sep. 20, 2023

(87) PCT Pub. No.: WO2022/204449
PCT Pub. Date: Sep. 29, 2022

(65) Prior Publication Data
US 2024/0181136 A1 Jun. 6, 2024

Related U.S. Application Data
(60) Provisional application No. 63/166,534, filed on Mar. 26, 2021.

(51) Int. Cl.
*A61L 27/52* (2006.01)
*A61L 27/54* (2006.01)

(52) U.S. Cl.
CPC ............... *A61L 27/52* (2013.01); *A61L 27/54* (2013.01); *A61L 2300/232* (2013.01); *A61L 2300/602* (2013.01); *A61L 2300/802* (2013.01)

(58) Field of Classification Search
None
See application file for complete search history.

(56) References Cited

U.S. PATENT DOCUMENTS 5,118,804 A * 6/1992 Defaye .................. C07H 15/04 536/120
2020/0181583 A1* 6/2020 Dupuy ........... C12Y 106/03001

OTHER PUBLICATIONS

A shear-induced network of aligned wormlike micelles in a sugar-based molecular gel. From gelation to biocompatibility assays, by Fitremann et al., Journal of Colloid and Interface Science, 2017, 504, pp. 721-730. (Year: 2017).*

(Continued)

*Primary Examiner* — Peter A Salamon
(74) *Attorney, Agent, or Firm* — Foley & Lardner LLP

(57) ABSTRACT

The present invention provides a biocompatible low molecular weight (LMW) hydrogel having a high storage modulus that comprises water and thioglycolipid. The invention also provides a carrier material and an article of manufacture comprising said LMW hydrogel. The present invention also provides methods for producing and using the same. The LMW hydrogels are made of aggregates of thioglycolipid via noncovalent interactions.

20 Claims, 16 Drawing Sheets a.

b.

c.

(56) References Cited

OTHER PUBLICATIONS

Simple Synthetic Molecular Hydrogels from Self-Assembling Alkylgalactonamides as Scaffold for 30 Neuronal Cell Growth, by Chalard et al., Applied Materials and Interfaces, 2018, 10, 17004-17017. (Year: 2018).*

Chirality inversion, supramolecular hydrogelation and lectin binding of two thiolactose amphiphiles constructed on a dilauroyl-L-tartaric acid scaffold, by Cano et al., New J. Chem, 2017, 41, 14754. (Year: 2017).*

Cano et al. 'Chirality inversion, supramolecular hydrogelation and lectin binding of two thiolactose amphiphiles constructed on a di-lauroyl-L-tartaric acid scaffold', New Journal of Chemistry, 2017, vol. 41(23), pp. 14754-14765.

Chalard et al. 'Simple Synthetic Molecular Hydrogels from Self-Assembling Alkylgalactonamides as Scaffold for 3D Neuronal Cell Growth', ACS Appl. Mater. Interfaces 2018, vol. 10, pp. 17004-17017.

Fitremann et al. 'A shear-induced network of aligned wormlike micelles in a sugar-based 1-31-molecular gel. From gelation to biocompatibility assays', Journal of Colloid and Interface Science, 2017, vol. 504, pp. 721-730; https://doi.org/10.1016/j.jcis.2017.06.021.

International Search Report and Written Opinion for PCT/US2022/021835 dated Jun. 16, 2022.

* cited by examiner

LOW MOLECULAR WEIGHT HYDROGELS COMPRISING THIOGLYCOLIPIDS

CROSS-REFERENCE TO RELATED APPLICATIONS

This application is a U.S. National Stage Application under 35 U.S.C. § 371 of International Patent Application No. PCT/US2022/021835, filed on Mar. 25, 2022, which claims the priority benefit of U.S. Provisional Application No. 63/166,534, filed Mar. 26, 2021, which are incorporated herein by reference in their entireties.

STATEMENT REGARDING FEDERALLY FUNDED RESEARCH

This invention was made with government support under grant numbers 1339597 and 1954467 awarded by the National Science Foundation. The government has certain rights in the invention.

FIELD OF THE INVENTION

The present invention relates to a non-cross-linked biocompatible low molecular weight (LMW) hydrogel having a high storage modulus. In some embodiments, the non-cross-linked biocompatible LMW hydrogel comprises water and thioglycolipid. The invention also relates to a carrier material and an article of manufacture comprising said LMW hydrogel. In particular, the present invention relates to low molecular hydrogels comprising thioglycolipids.

BACKGROUND OF THE INVENTION

Hydrogels have been utilized in many biomedical fields, including dermatology, drug delivery systems, stem cell delivery systems, bonding and coating systems, tissue engineering or repairing systems, wound healing, cell culture, etc. One current field of study is concerned with tissue and tissue manipulation using poly(ethylene glycol) (PEG) compounds. Another field of study is using biopolymer-based hydrogels as scaffolds or artificial extracellular matrices that provide growth spaces for cells from the viewpoint of tissue engineering. The scaffolds or artificial extracellular matrices allow cells to grow better or in desired directions for the purpose of tissue engineering.

Some of the biopolymers currently used for producing hydrogels include polysaccharides such as glycogen, chitosan, cellulose, and hyaluronic acid. These biopolymers are often converted into hydrogels by physical crosslinking or irreversible chemical crosslinking. The process of cross-linking biopolymers to produce hydrogels results in high molecular weight hydrogels and requires additional time and cost.

Unlike high molecular weight hydrogels, conventional low molecular weight (LMW) gels are composed of small molecules that aggregate via noncovalent interactions and generally form fibrous 3-D networks or porous structures that immobilize solvent. LMW gels do not need any cross-linking steps, and therefore, are less costly and time consuming to prepare. In addition, LMW gels are known to be thermoreversible, gel at lower concentrations, and have high tolerance towards salts. LMW hydrogels are some of the most unique gels, as they are mainly composed of water; this allows their potential use in diverse applications in soft materials and biomaterials including drug delivery, cell growth, enzyme immobilization, and tissue engineering. Therefore, much effort has focused on the design of small molecules that serve as low molecular weight hydrogelators as well as improving their physicochemical properties, such as mechanical properties and biocompatibility, for various applications. The gelation behavior and mechanical properties of hydrogels are difficult to predict given the complex processes of self-assembly and three-dimensional network formation, although approaches to tune their properties such as improving mechanical properties based on known hydrogels have been reported. Among all kinds of LMW gels, sugar-based gelators have gained special interest for use in novel soft materials due to their biodegradability and biocompatibility, as well as for their sourcing from renewable raw materials. Recently, glycolipid-based hydrogels have been used in neural cell cultures, scaffold for stem cells and enzymes, and as cell-responsive capsules, although this work is still in its infancy and optimization of systems and properties is required.

Sugars have long been of interest for use in functional low molecular weight hydrogels. However, common functional compositions utilizing sugars have either relied on complex gelator molecules to increase intermolecular interaction strength, with relatively complex chemical syntheses, or are based on materials harvested from natural sources requiring extensive effort. Furthermore, many conventional LMW hydrogels, including those made from certain sugar-based materials, are fibrous. More importantly, regardless of microstructure, most LMW hydrogels made from sugar-based materials have a relatively low mechanical strength, with minimal design guidelines emerging from past efforts on simple alkyl glycosides and related systems that could lead to stronger hydrogels.

Therefore, there is a need for a simple method of producing functional LMW hydrogels using readily available sources. In particular, there is a need for LMW hydrogels that have high mechanical strength and are not a fibrous 3-D network.

SUMMARY OF THE INVENTION

Surprisingly and unexpectedly, in contrast to other conventional LMW hydrogels based on glycolipids, many of which are fibrous, the present inventors have discovered that functional hydrogels (i.e., those possessing mechanical properties adequate for various commercializable uses) can be produced in a layered 3-D network by utilizing a specific set of disaccharide-based thioglycolipids. Moreover, LMW hydrogels of the invention have a surprisingly high mechanical strength compared to other conventional LMW hydrogels, including those based on glycolipids that have been reported previously. Accordingly, LMW hydrogels are applicable in a wide variety of applications including, but not limited to, biomedicine and environmental science. Particular examples of application that are suitable for LMW hydrogels of the invention include, but are not limited to, wound healing, tissue engineering and repair, drug delivery, cell culture, as markers for fluid flow or pollutant plume tracking, in heavy metal extraction, and oil spill remediation.

One particular aspect of the invention provides a biocompatible low molecular weight ("LMW") hydrogel. Some embodiments of the invention provide LMW hydrogels having a high storage modulus. In particular, LMW hydrogels of the invention are biocompatible. As used herein, the term "biocompatible" refers to substances that are not toxic to cells. For example, biocompatible can mean not producing a toxic, injurious, or immunologic response in living tissue, or the ability of a material to perform with an appropriate host response in a specific situation. In some embodiments, a substance is considered to be "biocompatible" if its addition to cells in vitro results in about 20% or less, typically about 10% or less, and often about 5% or less cell death. In other embodiments, a substance is considered to be "biocompatible" if its addition to cells in vivo does not induce inflammation and/or other adverse effects in vivo.

The term "LMW" refers to a compound or hydrogel having a molecular weight of about 1,500 g/mol or less, typically about 1,000 g/mol or less, and often about 750 g/mol or less.

Yet in other embodiments, the LMW hydrogels of the invention have a high storage modulus. The term "high storage modulus" refers to having a modulus of at least about 10 kPa, typically at least about 20 kPa, often at least about 50 kPa, and most often at least about 75 kPa at 25 °C. When referring to a numerical value, the terms "about" and "approximately" are used interchangeably herein and refer to being within an acceptable error range for the particular value as determined by one of ordinary skill in the art. Such a value determination will depend at least in part on how the value is measured or determined, e.g., the limitations of the measurement system, i.e., the degree of precision required for a particular purpose. For example, the term "about" can mean within 1 or more than 1 standard deviation, per the practice in the art. Alternatively, the term "about" when referring to a numerical value can mean ±20%, typically ±10%, often ±5% and more often ±1% of the numerical value. In general, however, where particular values are described in the application and claims, unless otherwise stated, the term "about" means within an acceptable error range for the particular value, typically within one standard deviation.

Still in other embodiments, the LMW hydrogels of the invention comprises water and thioglycolipid.

Other aspects of the invention provide a carrier material and an article of manufacture comprising the LMW hydrogel disclosed herein. Still other aspects of the invention provide methods for producing and using the same.

One particular aspect of the invention provides a biocompatible low molecular weight ("LMW") hydrogel having a high storage modulus, wherein said LMW hydrogel comprises water and thioglycolipid that are non-cross linked. In some embodiments, said hydrogel is a non-fibrous 3-D network. Still in other embodiments, at least 90% of said LMW hydrogel is water. Yet in other embodiments, the amount of thioglycolipid in said LMW hydrogel ranges from about 0.5% to about 10% by weight. In further embodiments, the storage modulus of said LMW hydrogel is at least about 10 kPa at 25 °C. In other embodiments, the storage modulus of said LMW hydrogel is at least about 100 kPa at 25 °C.

In one particular embodiment, said thioglycolipid comprises a disaccharide that is linked to a lipid via a thiol linkage. In general any disaccharides with 1→4 linkages known to one skilled in the art can be used. Particular examples of disaccharides used in the invention include, but are not limited to, lactose, maltose, cellobiose, lactulose, chitobiose or a combination thereof. For current cost considerations, typical disaccharides used include lactose, cellobiose, or a combination thereof.

Still in another embodiment, said thioglycolipid is of the formula: A-B, where A is a disaccharide sugar moiety that is linked to B through a thioether linkage, and B is $C_8$-$C_{20}$ n-alkyl. Exemplary alkyls used in the invention include, but are not limited to, $C_8$ alkyl, $C_{10}$ alkyl, $C_{12}$ alkyl, $C_{14}$ alkyl, $C_{16}$ alkyl, $C_{18}$ alkyl, and $C_{20}$ alkyl.

Another aspect of the invention provides a carrier material comprising (a) a LMW hydrogel disclosed herein and (b) a cargo. In some embodiments, said cargo is a therapeutic agent or prophylactic agent. In some instances, said therapeutic agent or prophylactic agent is a nutrient, pharmaceutical, drug, prodrug, peptide, glycopeptide, enzyme, polynucleotide, lipid, phospholipid, co-surfactant, metal complexant, steroid or other anti-inflammatory agent, antibacterial agent, antifungal agent, disinfecting agent, or combinations thereof.

Yet in other embodiments, said cargo is an absorbing material, a substrate in tissue engineering or cell culture.

Another aspect of the invention provides an article of manufacture comprising a LMW hydrogel disclosed herein. In some embodiments, said article of manufacture comprises a wound healing material, tissue engineering or repair material, cell culture material, or controlled-release drug delivery material. Yet in other embodiments, said article of manufacture comprises microparticles or nanoparticles of the LMW hydrogel, and wherein the microparticles or nanoparticles of LMW hydrogel comprises a cargo. In some instances, said cargo is a therapeutic agent, a prophylactic agent, an indicator moiety, a labelling moiety, an environmental tracer, a complex-forming agent that forms a complex with a heavy metal or a rare earth element, or an agrochemical. In other instances, said cargo comprises a rhamnolipid, a mono- or disaccharide analogue, or a combination thereof. Still in other instances, said cargo is a therapeutic agent.

Yet another aspect of the invention provides an article of manufacture comprising a microparticle or a nanoparticle, wherein said microparticle or a nanoparticle comprises a core and a shell, and wherein said core comprises a magnetic material and said shell comprises the LMW hydrogel disclosed herein and a cargo. In some embodiments, said core comprises iron, nickel, cobalt, or a combination thereof.

Still another aspect of the invention provides a low molecular weight physical hydrogel comprising water and thioglycolipid having a storage modulus of at least about 10 kPa at 25 °C, wherein said hydrogel comprises at least about 80% by weight of water. In some embodiments, said hydrogel comprises at least about 90% by weight of water. Still in other embodiments, said hydrogel comprises at least about 1% by weight of thioglycolipid. Yet in other embodiments, said hydrogel comprises at least about 2% by weight of thioglycolipid. In further embodiments, said hydrogel comprises at least about 5% by weight of thioglycolipid.

Still in further embodiments, said thioglycolipid is of the formula: A-B, where A is a disaccharide sugar moiety that is linked to B through a thioether linkage, and B is $C_8$-$C_{20}$ alkyl. In some instances, B comprises $C_8$ alkyl, $C_{10}$ alkyl, $C_{12}$ alkyl, $C_{14}$ alkyl, $C_{16}$ alkyl, $C_{18}$ alkyl, or $C_{20}$ alkyl.

Yet in other embodiments, a storage modulus (G') of said low molecular weight physical hydrogel ranges from about 10 kPa to about 570 kPa.

DETAILED DESCRIPTION OF THE INVENTION

Figure 1:
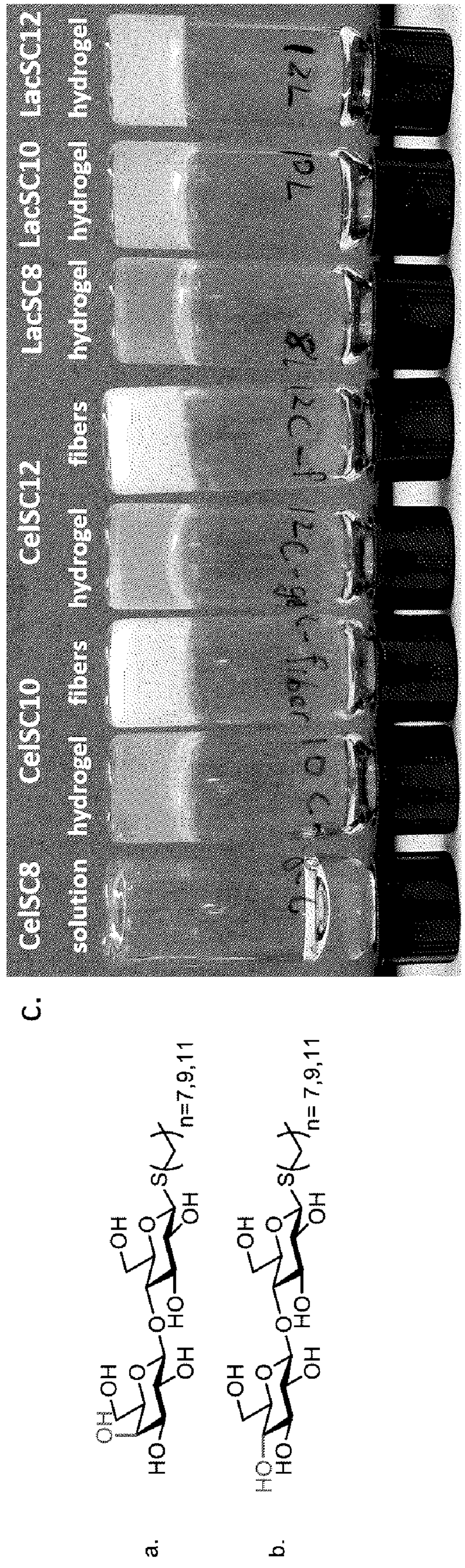
FIG. 1 shows molecular structures of a) alkyl-β-thiolactosides and b) alkyl-β-thiocellobiosides, and c) pictures CelSC8 solution and gel formation for CelSC10, CelSC12, LacSC8, LacSC10, and LacSC12.

Some aspects of the present invention are based on development of a series of low molecular weight hydrogels based on simple alkyl glycolipids by the present inventors. The alkyl glycolipids are readily produced in large quantities through a scalable, high-yield synthetic process that provides tailoring of LMW hydrogel properties. Despite being held together through non-covalent interactions, these hydrogels exhibit mechanical strengths with storage moduli up to 10's to 100's of kPa in contrast to the 1,000's of Pa typical of other non-cross-linked hydrogels. These features facilitate potential utility of these hydrogels in a range of applications. Some of the advantages of LMW hydrogels of the invention include, but are not limited to, (i) their production by a simple, scalable, high-efficiency process with short formation time, (ii) direct hydrogel formation in water only without the need for additives, organic solvents or salts, (iii) resistance to acidic and basic environments and added salts, (iv) stability at body temperature without the need for cross linking, and (v) biocompatible and biodegradable since these materials are based on sugars.

In some embodiments, the LMW hydrogels of the invention can be made from simple alkyl thioglycolipids that spontaneously self-assemble through weak, noncovalent intermolecular interactions. The LMW hydrogels of the invention are formed rapidly from the alkyl thioglycolipids disclosed herein, have surprising and unexpected mechanical strength, and are biocompatible and biodegradable. LMW hydrogels of the invention can be used in a wide range of applications including, but not limited to, biomedicine to environmental science.

The invention provides a series of LMW hydrogels from simple glycolipids that possess surprising mechanical strength and stability at human body temperatures despite being self-assembled through noncovalent interactions. Moreover, these LMW hydrogels are thixotropic (rapidly and fully self-healing back to original storage moduli values) after repeated exposure to shear stress. Because LMW hydrogels are biocompatible and biodegradable, they are especially suitable for applications ranging from biomedicine to environmental science. For example, in the biomedical arena, LMW hydrogels of the invention can be used in a range of ex vivo and in vivo applications such as, but not limited to, wound healing, tissue engineering and repair, drug delivery, and cell culture. In the environmental applications, LMW hydrogels of the invention (e.g., in microparticle or nanoparticle form) can be used, for example, as markers for fluid flow or pollutant plume tracking, in heavy metal extraction, and oil spill remediation.

One particular aspect of the invention provides a biocompatible low molecular weight ("LMW") hydrogel having a high storage modulus, wherein said LMW hydrogel comprises water and thioglycolipid. In some embodiments, the molecular weight of the thioglycolipid is 750 g/mol or less.

Still in other embodiments, the LMW hydrogel is non-cross-linked hydrogel. Yet in other embodiments, the storage modulus of LMW hydrogel is at least 10 kPa at 25 °C.

In other embodiments, at least about 80%, sometimes at least about 85%, typically at least about 95%, and often at least about 98% of said LMW hydrogel is water. Yet in other embodiments, the amount of thioglycolipid in said LMW hydrogel ranges from about 0.25% to about 20% by weight, typically from about 0.5% to about 10% by weight, and often from about 0.5% to about 5% by weight. Still in other embodiments, the storage modulus of said LMW hydrogel at 25 °C is at least about $10^5$ Pa, typically at least about 10 kPa, more often at least about 20 kPa, and more often at least about 50 kPa, and most often at least about 75 kPa.

Still in other embodiments, the thioglycolipid comprises a thiol derivative of disaccharide. As used herein, the term "thiol derivative" refers to having a sugar moiety that is attached to a lipid moiety via a thioether linkage. The thiol moiety can be derived from the functional group of the lipid moiety or the sugar moiety.

In some embodiments, the LMW hydrogel comprises a mixture of a thioglycolipid and a glycolipid. In these embodiments, the amount of thioglycolipid can range from about 1% to about 99%, typically from about 5% to about 95%, often from about 5% to about 75%, more often from about 5% to about 50%, still more often from about 5% to about 25%, and most often from about 5% to about 10%. In other embodiments, the amount of glycolipid can range from about 1% to about 99%, typically from about 5% to about 95%, often from about 5% to about 75%, more often from about 5% to about 50%, still more often from about 5% to about 25%, and most often from about 5% to about 10%.

In one particular embodiment, the disaccharide comprises lactose, maltose, cellobiose, lactulose, chitobiose, or a combination thereof.

Yet in some embodiments, the thioglycolipid and/or the glycolipid is of the formula: A-B, where A is a sugar moiety (typically a disaccharide) and B is a lipid moiety such as $C_8$-$C_{20}$ alkyl. It should be appreciated that in thioglycolipids A and B are linked through a sulfur atom (i.e., thioether) linkage, whereas in glycolipids A and B are linked through an oxygen atom (i.e., ether) linkage. In some embodiments, B comprises $C_8$ alkyl, $C_{10}$ alkyl, $C_{12}$ alkyl, $C_{14}$ alkyl, $C_{16}$ alkyl, $C_{18}$ alkyl, or $C_{20}$ alkyl.

Another aspect of the invention provides a carrier material comprising (a) a LMW hydrogel disclosed herein and (b) a cargo. In some embodiments, the cargo comprises a therapeutic agent, including a wound healing material, or prophylactic agent. In general, a therapeutic agent refers to any drug or a prodrug known to one skilled in the art that is used to treat a clinical condition, disease, or a disorder in a subject. Typically, the subject is mammal, and often human. Exemplary therapeutic agents include drugs and biologics that have been approved by the Food and Drug Administration (FDA) for human or animal use, any drugs or biologics that are currently undergoing a clinical trial, and other drugs and biologics that are or will be developed for treatment of human or animals.

In some embodiments, the therapeutic agent is independently selected from the group consisting of an anticancer agent, an antiviral agent, an antibacterial agent, antifungal agent, an immunosuppressant agent, a hemostasis agent, and an anti-inflammatory agent.

Cell based therapies are important options for the treatment of clinical indications including diseases, tissue damage, neurological disorders, blood disorders, cancers, developmental defects, wounds and orthopedic impediments. Many cell-based therapies are target specific, with cells being administered directly to a target site. When cells are not suitably retained at a target site after administration, there is both a loss of cells available for the intended treatment as well as an increased risk of cell differentiation at an alternative site. When cells are administered to a target site without sufficient protection, the cells may go through physiochemical changes such as hypertrophy, necrosis, apoptosis, or senescence. Treatment efficacy is attenuated when the administered cells are physiochemically altered or not retained at the desired target site. In one particular embodiment of the invention, LMW hydrogels of the invention can be used to deliver cells to a desired therapeutic target area. In another embodiment, the LMW hydrogels can be used to deliver nutrients to cells within a desired target area.

In certain embodiments, the carrier can be prepared by admixing the precursor of LMW hydrogel and the cargo in an aqueous solution. In some embodiments, gelling or the formation of LMW hydrogel comprising the cargo can be controlled by time, the pH of the aqueous buffer, and/or other factors such as temperature, concentration, etc. In one particular embodiment, the gelling time (i.e., formation of LMW hydrogel comprising a cargo) ranges from about 20 seconds to about 30 minutes, typically, from about 1 minute to about 20 minutes.

In some embodiments, the cargo is released from the LMW hydrogel through diffusion, osmosis, degradation of the LMW hydrogel, including enzymatic degradation, or any combination thereof. In certain embodiments, the cargo is initially released from the LMW hydrogel through diffusion and later released through degradation of the LMW hydrogel. In some embodiments, the cargo is substantially released from the LMW hydrogel within one day, typically within 24 hours, often within 12 hours, and most often within 8 hours. In some embodiments, the LMW hydrogel precursor or the LMW hydrogel and the cargo do not form a covalent bond or cross-link during formation of the carrier. Yet in other embodiments, the LMW hydrogel precursor (e.g., thioglycolipid) or LMW hydrogel and the cargo form a covalent bond or become cross-linked during formation of the carrier.

The carrier can be made by mixing (a) LMW hydrogel precursor disclosed herein with (b) a cargo in an aqueous solution under conditions sufficient to form a carrier comprising a LMW hydrogel and a cargo. Alternatively, the carrier can be made using a droplet microfluidic. Exemplary method for using a droplet microfluidic can be found, for example, in U.S. Pat. No. 7,485,671, issued to Qiu et al. on Feb. 3, 2009, which is incorporated herein by reference in its entirety.

In some embodiments, the therapeutic agent or prophylactic agent is a nutrient, pharmaceutical, drug, prodrug, peptide (including polypeptide and protein), glycopeptide, enzyme, polynucleotide, lipid, phospholipid, co-surfactant, metal complexant, steroid or other anti-inflammatory agent including NSAID, antibacterial agent, antifungal agent, disinfecting agent, or combinations thereof. The terms "polynucleotide" and "oligonucleotide" are used interchangeably herein and refer to a deoxyribonucleotide or ribonucleotide polymer in either single- or double-stranded form, and unless otherwise limited, encompasses known analogs of natural nucleotides that hybridize to nucleic acids in a manner similar to naturally-occurring nucleotides. Examples of such analogs include, without limitation, phosphorothioates, phosphoramidates, methyl phosphonates, chiral-methyl phosphonates, 2-O-methyl ribonucleotides, and peptide-nucleic acids (PNAs).

Still in other embodiments, the cargo is an absorbing material or a substrate in tissue engineering or cell culture.

Another aspect of the invention provides an article of manufacture comprising a LMW hydrogel disclosed herein. In some embodiments, the article of manufacture comprises a wound healing material, tissue engineering or repair material, cell culture material, or controlled-release drug delivery material. Yet in other embodiments, the article of manufacture comprises microparticles or nanoparticles of the LMW hydrogel, where the micro- or nanoparticles of LMW hydrogel contain a cargo. In some embodiments, the cargo is a therapeutic or prophylactic agent including those disclosed herein. Still in other embodiments, the cargo is an indicator moiety, a labelling moiety, an environmental tracer, or a complex-forming agent that forms a complex with a heavy metal or a rare earth element. In one particular embodiment, the cargo comprises a rhamnolipid or an analogue of a rhamnolipid based on a different sugar. Yet in other embodiments, the cargo is an agrochemical. Exemplary agrochemicals that can be used in the invention include, but are not limited to, a fertilizer or other agricultural nutrient, herbicide, pesticide, biocide, fungicide, sporocide, and combinations thereof. In one particular embodiment, the article of manufacture comprises a controlled-release agrochemical delivery material.

The article of manufacture can be used in a variety of applications depending on the nature of the cargo. In some embodiments, the article of manufacture is used as a therapeutic agent. In other embodiments, the article of manufacture is used as an environmental bioremediation or sequestering agent. Yet in other embodiments, the article of manufacture is used as a metal harvesting agent.

Yet another aspect of the invention provides an article of manufacture that comprises a microparticle or a nanoparticle having a core and a shell. The core comprises a magnetic material and the shell comprises a LMW hydrogel. In some embodiments, the LMW hydrogel comprises a cargo. The cargo can be any one or more of the cargo as described herein. In certain embodiments, the core comprises iron, nickel, cobalt, or a mixture thereof.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Materials. The thioglycolipids were synthesized via methodology previously reported by one of the present inventors with a modified deacetylation procedure. Szabó et al., *Carbohydr. Res.* 2016, 422, 1-4. https://doi.org/10.1016/j.carres.2015.12.008

Acetylation of sugars. To an oven-dried round bottom flask equipped with a stir bar were added sugar (1 eq) and sodium acetate (0.37 eq). The round bottom flask was evacuated and refilled with dry nitrogen. Anhydrous toluene (20 mL/mmol of sugar) and acetic anhydride (1.7 eq/OH of sugar) were then added via syringe. The contents of the round bottom flask were stirred and refluxed at 120 °C for 24 hours until the reaction was complete as indicated by TLC analysis. The reaction mixture was then cooled to room temperature. Water (10 mL/mmol of sugar) was then added to the reaction mixture. The contents of the round bottom flask were stirred for 1 hour. Then, diethyl ether (30 mL/mmol of sugar) was added to the reaction. The stirring was continued until white solid precipitated. Suction filtration was used to collect the products. Recrystallization by ethanol was then performed to give pure products.

Glycosylation of sugars with primary alkyl thiols. To an oven-dried round bottom flask equipped with a stir bar were added sugar octaacetate (1 eq) and indium bromide (3 wt %). The round bottom flask was evacuated and refilled with dry nitrogen. Anhydrous chloroform (5 mL/mmol of sugar octaacetate) and alkylthiol (2 eq) were then added via syringe. The contents of the round bottom flask were stirred and refluxed at 60 °C for 24 hours until the reaction was complete as indicated by TLC analysis. The reaction mixture was then cooled to room temperature and extracted with chloroform. The combined organic layers were washed three times with copious amounts of water and dried over magnesium sulfate. The organic phase was condensed by evaporation, and the resulting residue was purified by column chromatography on silica gel to give the product.

De-acetylation of acetyl glycolipids. To an oven-dried round bottom flask equipped with a stir bar were added alkyl-β-thioperacetyl sugar (1 eq) and Amberlyst resin (35 wt % of alkyl-β-thioperacetyl sugar). Methanol was then added to the mixture. The contents of the round bottom flask were stirred for 24 hours until the reaction was complete as indicated by TLC analysis. Gravity filtration was then performed to separate the resin from the organic phase. The organic phase was then condensed by evaporation. The chemical structures of the final compounds were characterized by $^{1}$H NMR, $^{13}$C NMR and mass spectrometry.

Preparation of Thioglycolipid Solutions and Hydrogel Fabrication. Aqueous solutions of thioglycolipids were prepared by weighing 2-3 mg of thioglycolipids and adding an appropriate volume of water to make solution samples at desired concentrations in vials. The vials were capped, sealed with Parafilm, and heated to 75 °C (or 85 °C for $LacSC_{12}$) until the thioglycolipids were completely dissolved, which typically required about 1 min. The samples were then allowed to cool to ambient temperature. Above some minimal concentration, the solution forms hydrogels upon cooling (FIG. 1). While hydrogelation happens in under 1 min, the gels were allowed to equilibrate at room temperature for 15 min before any analysis. To make metastable thiocellobiosides gels, the samples were quenched at −4 °C after dissolution at 75 °C. Although the metastable hydrogels also formed in under 1 min, the gels were allowed to equilibrate at −4 °C for 15 min before analysis.

A similar protocol for hydrogelation as described above was used to make cargo-containing gels for analysis. In this case, water was replaced with a dilute aqueous solution of the cargo.

Differential Scanning calorimetry. A Mettler Toledo DSC 823e differential scanning calorimeter, equipped with cooling apparatus, was used for measurement of the phase transition temperature and enthalpy of the gels. Hydrogel samples were first prepared using the fabrication method described above. Then, they were heated to 75 °C (or 85 °C for $LacSC_{12}$) until they were in the solution state and then pipetted into aluminum, 40 μL DSC pans and capped with lids. The amount of hydrogel in each aluminum pan was controlled to about 6-8 mg. The pans were maintained at 85 °C for 1 min to ensure the samples were in the solution state. Then, they were cooled to 5 °C and maintained at this temperature for 20 min to ensure the formation of hydrogels.

On subsequent cooling, the samples were heated from 5 °C to 85 °C at a heating rate at 5 °C per min.

Rheometry. The viscoelastic mechanical properties of the hydrogels were characterized using small amplitude oscillatory shear rheology on a Discovery Hybrid Rheometer 2 (TA Instruments, USA) with a sandblasted 20 mm cone-and-plate geometry at a 1° angle and a sandblasted stage. Inertia, friction, and rotational mapping calibrations were performed prior to each experiment. A Peltier temperature-controlled stage was maintained at 4 °C, 10 °C, 25 °C, or 37 °C for rheology testing. Hydrogels were heated in a water bath above their transition temperature for 5 min, then transferred to the stage before the geometry was lowered quickly (1-3 sec) to the testing gap height of 50 μm. Excess gel was trimmed from the edges of the assembly. To control evaporation, the assembly was encased in a solvent trap with a water seal, and a mineral oil barrier was placed around the edges of the trap. Hydrogels were allowed to form and relax for 1 hour prior to experimentation. Strain sweeps were performed from 0.01% to 1000% shear strain at a constant 10 rad/s angular frequency. G' (storage modulus) and G" (loss modulus) were determined by averaging data within the linear viscoelastic region of the strain sweep. Frequency sweeps were performed from 0.01 rad/s to 100 rad/s at a constant 0.01% shear strain. Thixotropy experiments were conducted by cycling the shear strain between 0.01% and 100%.

Electron Microscopy. Scanning electron microscopy (SEM) was performed on an FEI Inspect S SEM equipped with a tungsten filament and a secondary electron detector for standard imaging. The preparation of xerogel samples for SEM analysis is described as follows: hydrogel samples were first heated to the solution state and then pipetted onto SEM sample stubs. Sample stubs containing the thiolactosides were then cooled at room temperature for 15 min for hydrogelation. For hydrogels from thiocellobiosides, the sample stubs with solution were quenched in at −4 °C ice/water bath for 15 min to form hydrogels. Then, samples were flash-frozen in liquid nitrogen followed by lyophilization to yield xerogels. Samples were gold coated prior to SEM characterization to reduce sample charging.

A Hitachi HF-5000 Transmission Electron Microscope (TEM) was used for TEM analysis to probe nanostructure of the xerogels. The preparation of xerogel samples for TEM is described as follows: lyophilization was performed after hydrogelation in 1-dram vials. After lyophilization, hexane was added to the vial followed by sonication for several seconds. Then, 1 μL of the resulting solution was pipetted onto a TEM grid. The grid was allowed to dry overnight prior to TEM imaging.

Fluorescence Spectroscopy. Steady-state fluorescence spectroscopy was performed on a Photon Technologies, Inc. (PTI), Quanta Master 40 spectrofluorometer. Prodan fluorescence was excited at 350 nm with emission observed between 370 nm and 640 nm. $LacSC_8$, $LacSC_{10}$, $LacSC_{12}$, $CelSC_8$, $CelSC_{10}$ and $CelSC_{12}$ gels and solutions were studied. Fluorescence spectra were initially acquired at 5 °C.

Then, using a 10 °C increment, fluorescence spectra were acquired between 5 °C and 75 °C for all thioglycolipids except $LacSC_{12}$, which was studied to 85 °C. Given the optical opacity of the gels, fluorescence spectra were acquired in a front face illumination geometry. Hydrogel samples containing the fluorophore prodan were first heated to the solution state, pipetted into a 1.7 mL-triangular fluorescence cuvette (Wilmad Lab-Glass) and then capped with a stopper to prevent evaporation. The cuvette was then quenched either at room temperature or at −4 °C to form hydrogels, and the sample allowed to equilibrate for 30 min prior to spectral acquisition. For samples that remain as solutions under all conditions, a similar preparation method was employed for characterization using a right-angle geometry, but a 10 mm-path rectangular fluorescence cell (Starna cell) was used instead. Normal right-angle fluorescence sampling was only conducted on 1 wt % $LacSC_8$ and 1 wt % $CelSC_{10}$ samples that were visually clear.

Visual Assessment of Thioglycolipid Hydrogel Formation. A wide range of thioglycolipid solutions were evaluated to establish concentration conditions (wt %) under which hydrogelation occurs and to assess the formation of other phases. Visual assessments of these aqueous solutions for different concentration conditions at room temperature are summarized in Table 1. For $LacSC_8$ and $LacSC_{12}$ solutions at concentrations <0.5 wt %, the solutions were either clear (C) or contain large aggregates (O) (i.e., cloudy). These solutions formed partial hydrogels surrounded by clear solution between 0.5 but <1 wt %, and were completely gelled at concentrations of 1 wt % and greater. Solutions of $LacSC_{10}$ at <2 wt % formed partial hydrogels surrounded by clear liquid but were completely gelled at or above 2 wt %. $CelSC_8$ solutions remained as clear solutions at all concentrations studied. $CelSC_{10}$ and $CelSC_{12}$ solutions formed settled fibrous aggregates in clear solution after equilibrating at ambient temperature overnight. However, $CelSC_{10}$ and $CelSC_{12}$ solutions completely hydrogelled when quenched at temperatures <20 °C, although these slowly transformed into settled fibrous aggregates over time at room temperature, suggesting that they are metastable. If retained at 5 °C, the $CelSC_{10}$ and $CelSC_{12}$ gels were stable for at least 6 months. Interestingly, the metastable fibrous hydrogel structure was maintained, even in inverted vials, but any vibrational perturbation caused these fibrous gels to readily expel their water. Powder x-ray diffraction confirmed that these fibrous aggregates were crystalline. Overall, the thioglycolipid concentration at which hydrogelation can be observed can be as low as 0.05 wt %, depending on thioglycolipid system, compared to the typical concentration for hydrogelation of at least 1 wt % commonly reported in the literature, although 0.25-2 wt % is the concentration range wherein these thioglycolipid solutions became fully hydrogelled. The existence of metastable hydrogels and the ability to tune the transformation of hydrogels into crystals may allow their potential use as smart materials for different applications.

TABLE 1

Visual assessment of aggregation and gelation of thioglycolipids at room temperature.

| | Thioglycolipid Concentration, wt % | | | | | | | | |
|---|---|---|---|---|---|---|---|---|---|
| Thioglycolipid | 0.05 | 0.1 | 0.25 | 0.5 | 0.75 | 1 | 2 | 5 | 10 |
| LacSC8 | C | C | C | G + C | G + C | G | G | G | G |
| LacSC10 | G + C | G + C | G + C | G + C | G + C | G + C | G | G | G |

TABLE 1-continued

Visual assessment of aggregation and gelation of thioglycolipids at room temperature.

| | Thioglycolipid Concentration, wt % | | | | | | | | |
|---|---|---|---|---|---|---|---|---|---|
| Thioglycolipid | 0.05 | 0.1 | 0.25 | 0.5 | 0.75 | 1 | 2 | 5 | 10 |
| LacSC12 | O | O | O | G + C | G + C | G | G | G | G |
| CelSC8 | C | C | C | C | C | C | C | C | C |
| CelSC10 | F | F | G or F | G or F | G or F | G or F | G or F | G or F | G or F |
| CelSC12 | F | F | G or F | G or F | G or F | G or F | G or F | G or F | G or F |

G = gel, F = fibrous aggregation, C = clear solution, O = cloudy solution.

Thermal Properties by DSC. Differential scanning calorimetry (DSC) was used to determine the phase transition temperature as well as to explore the possible existence of other lyotropic phases. DSC involves monitoring the enthalpy change during a phase transition, which can be used as a measure of hydrogel stability. The results (Table 2) indicated an endothermic transition between 30 °C and 80 °C. for all thioglycolipid hydrogels studied, and these transitions matched those observed visually in bulk solutions. Overall, hydrogels with longer carbon chains had higher thermostability (i.e., higher phase transition temperature). In addition, the $LacSC_x$ (x=10,12) hydrogels had higher thermostability than the $CelSC_x$ (x=10,12) hydrogels, despite similar phase transition enthalpies. $LacSC_8$, $LacSC_{10}$ and $CelSC_{10}$ hydrogels exhibited similar enthalpies for the gel-sol transition. However, the $LacSC_{12}$ and $CelSC_{12}$ hydrogels required twice the enthalpy compared to the other three. Collectively, these results suggest that thioglycolipid chain length is the determining contributor to hydrogel thermostability.

TABLE 2

Differential Scanning Calorimetry results.

| | Thioglycolipid and Concentration | | | | |
|---|---|---|---|---|---|
| | 1 wt % LacSC8 | 2 wt % LacSC10 | 1 wt % LacSC12 | 1 wt % CelSC10 | 1 wt % CelSC12 |
| Phase transition temperature | 38-46° C. | 57-64° C. | 63-79° C. | 31-37° C. | 42-54° C. |
| Enthalpy (J/g hydrogel) | 0.20 ± 0.03 | 0.35 ± 0.02 | 0.39 ± 0.10 | 0.18 ± 0.01 | 0.42 ± 0.06 |
| Enthalpy (kJ/mol thioglycolipids) | 9.2 ± 1.4 | 8.8 ± 0.5 | 20.7 ± 5.3 | 9.0 ± 0.6 | 22.3 ± 3.3 |

Mechanical Properties by Rheology. Viscoelasticity is an important property of hydrogels, as different mechanical properties dictate utility in different applications. Rheology was used to characterize the viscoelastic properties of these thioglycolipid hydrogels. The two parameters of interest in these studies were storage modulus (G') and loss modulus (G"). Materials for which G'>G" are considered more solid-like, the desired behavior for hydrogels; in contrast, systems for which G">G' are considered more liquid-like. The magnitude of G' is also an important parameter, as different hydrogel applications require different storage moduli. For instance, hydrogel scaffolds used for the replacement of functional tissues such as cardiovascular or musculoskeletal connective tissues require hydrogels with G'>1 kPa; similarly, stiff peptide hydrogels with G'>10 kPa are candidates for tissue engineering applications.

Figure 2A:
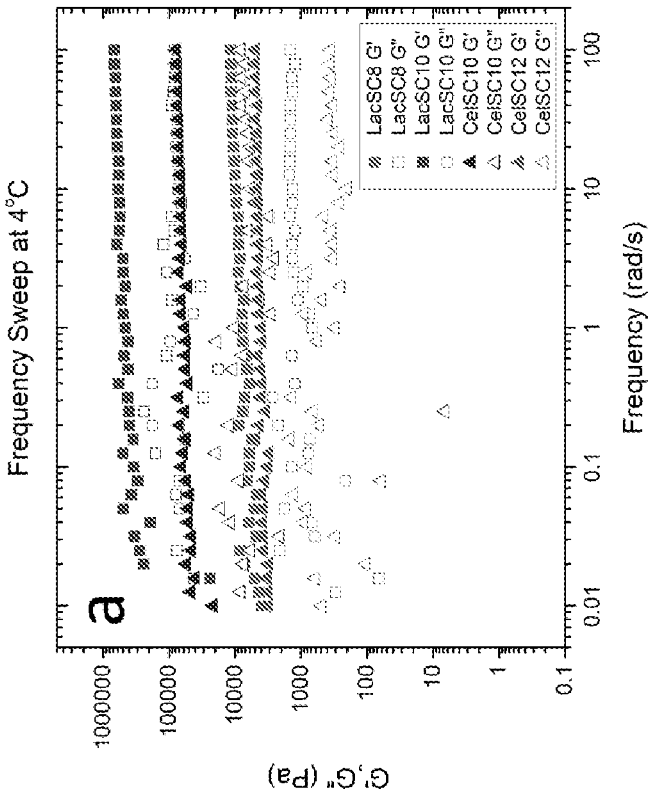
FIG. 2A shows representative rheology results for thioglycolipid hydrogels at 4 °C frequency sweeps.
Figure 2B:
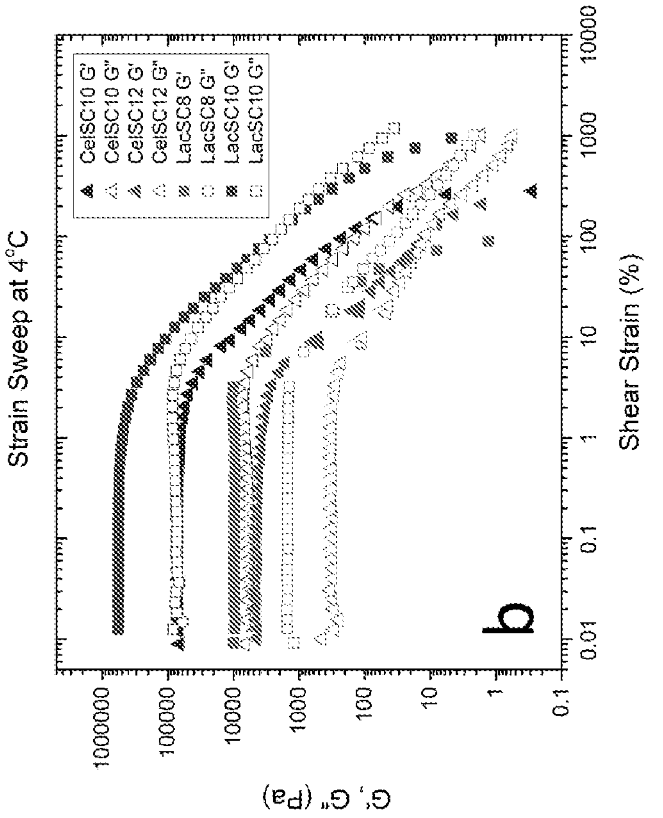
FIG. 2B shows representative rheology results for thioglycolipid hydrogels at 4 °C strain sweeps.
Figure 2C:
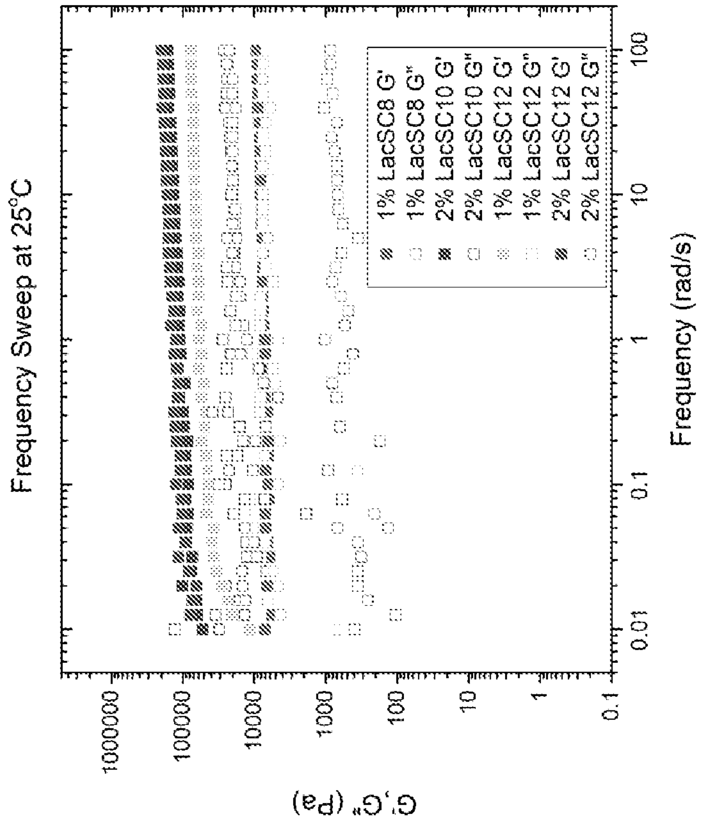
FIG. 2C shows representative rheology results for thioglycolipid hydrogels at 25 °C frequency sweeps.

Strain sweep experiments were conducted on thioglycolipid hydrogels from 0.01% to 1000% shear strain at a constant 10 rad/s angular frequency at different temperatures, and frequency sweep experiments were performed from 0.01 rad/s to 100 rad/s at a constant 0.01% shear strain. All samples tested were at 1 wt % concentration except $LacSC_{10}$ which was studied at 2 wt % given its required higher concentration for full gelation. All hydrogels tested exhibited solid-like behavior under certain conditions (FIGS. 2A and 2C). For the metastable $CelSC_{10}$ and $CelSC_{12}$ gels, rheology was only performed at 4 °C and 10 °C, the temperature range for which these hydrogels remain metastable without crystallization. Rheology was performed on the $LacSC_{10}$ gels at 4 °C, 25 °C and 37 °C. The $LacSC_8$ hydrogel was only studied at 4 °C and 25 °C, because 37 °C is above this gel's phase transition temperature. Although $LacSC_{12}$ hydrogels are stable at 4 °C, rheology was not performed at 4 °C, as this material formed hydrogels too quickly, rendering consistent sample transfer challenging.

Figure 2D:
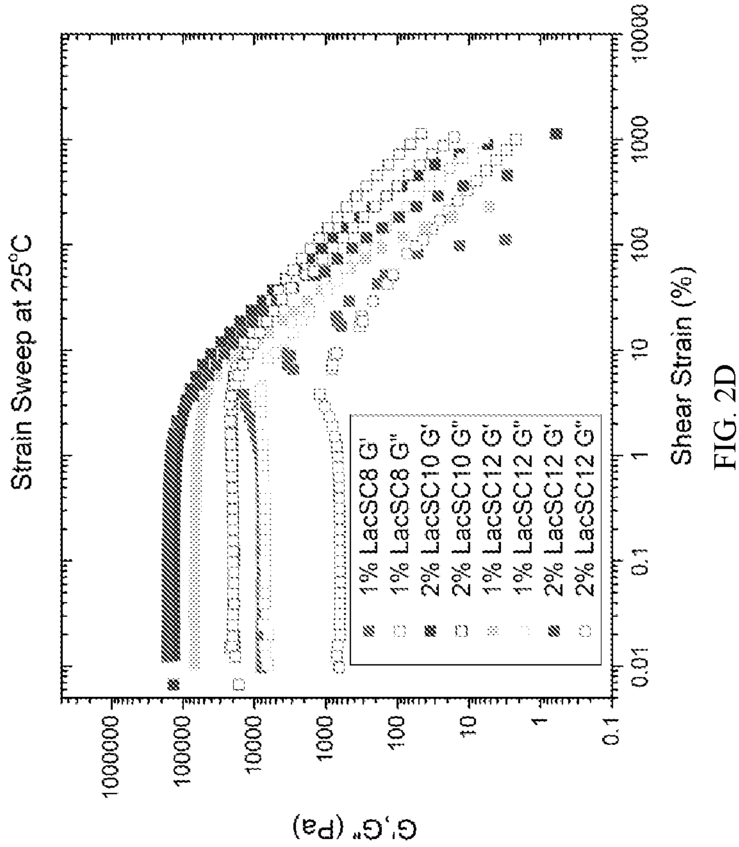
FIG. 2D shows representative rheology results for thioglycolipid hydrogels at 25 °C strain sweeps.

The rheology crossover point was generally observed between 50% and 100% shear strain for these materials (FIGS. 2B and 2D) with a few samples that had a crossover point slightly beyond 100%, (e.g., $CelSC_{10}$, $CelSC_{12}$, $LacSC_{10}$ at 4 °C and $LacSC_{10}$ at 10 °C). Overall, as the temperature decreased, values of both storage modulus (G') and crossover point increased due to strengthening of the noncovalent interactions. Therefore, enhancement of the mechanical properties was observed as temperature was decreased. Hydrogels of both $CelSC_{10}$ and $LacSC_{10}$ have G" values higher than those of $CelSC_{12}$ and $LacSC_{12}$. In total, these results demonstrate that the thioglycolipids of the invention can act as a hydrogelators with G' values up to $10^2$-$10^3$ kPa.

Figure 2F:
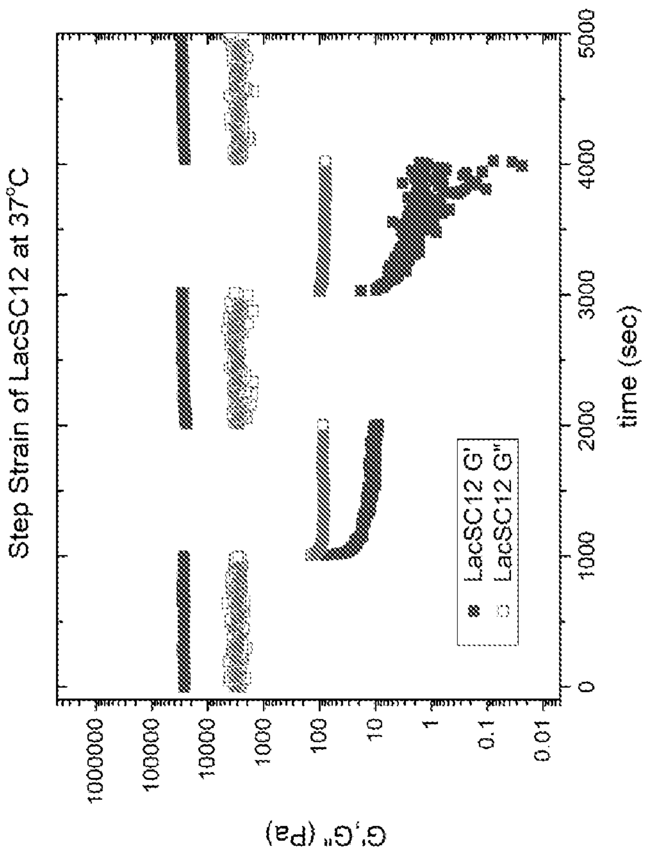
FIG. 2F shows representative rheology results of step strain experiments for $LacSC_{12}$.
Figure 2E:
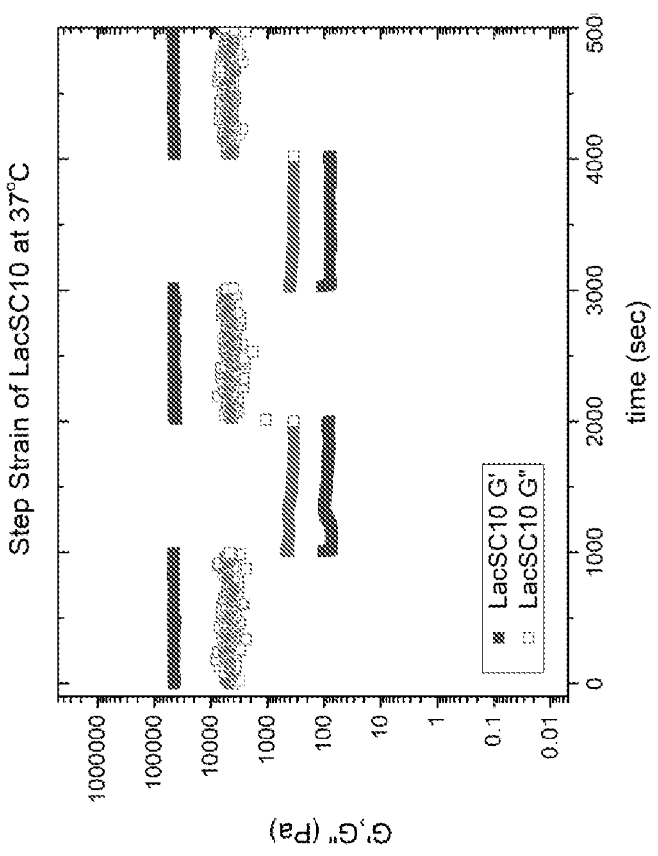
FIG. 2E shows representative rheology results of step strain experiments for $LacSC_{10}$.

Among all hydrogels tested, $LacSC_{10}$ and $LacSC_{12}$ hydrogels retained their gel properties at 37 °C, making these gels candidates for medical applications. Thixotropy experiments were conducted by cycling the shear strain between 0.01% and 100%, and the results validated the self-healing properties of these two hydrogels (FIGS. 2E and 2F). The results indicated a rapid recovery of gel properties of these materials after the shear force is released. The 1 wt % $LacSC_{12}$ broke more slowly upon application of shear force given its higher crossover point. However, the $LacSC_{12}$ hydrogel broke more completely than the $LacSC_{10}$ hydrogel, as its G' value continued to decrease with time after the shear force was removed. Both $LacSC_{12}$ and $LacSC_{10}$ hydrogels recovered almost immediately as the shear force was removed.

Figure 2G:
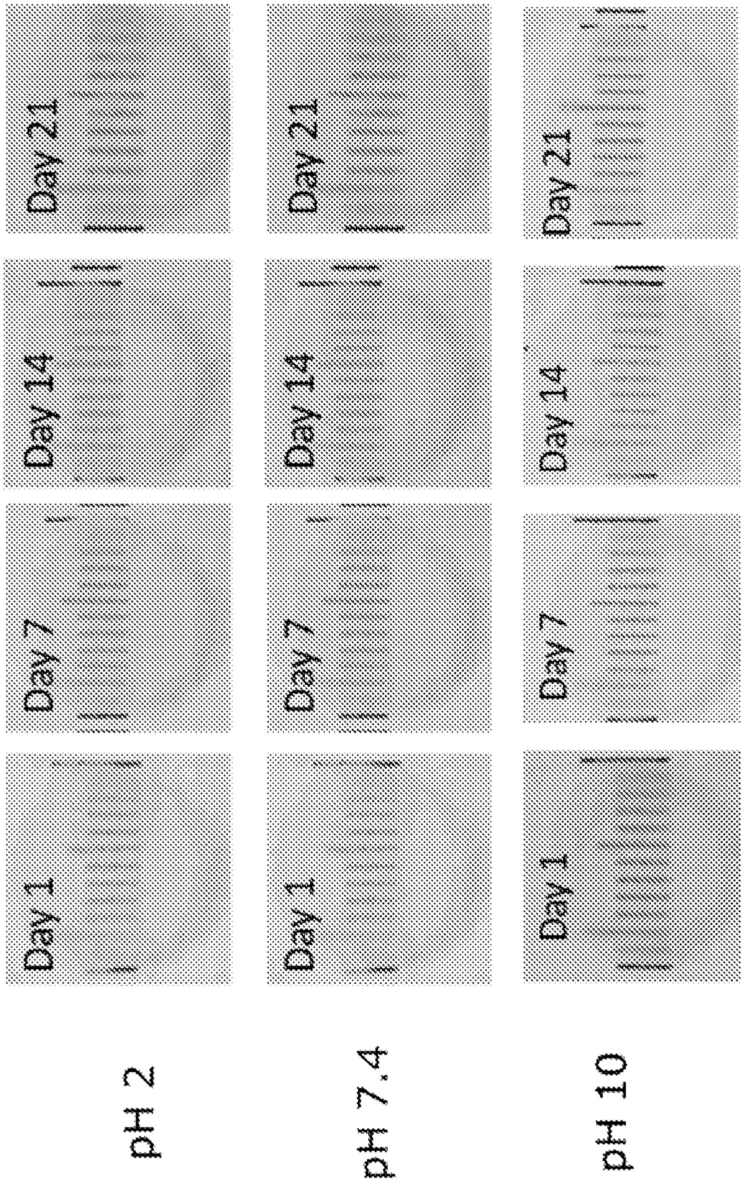
FIG. 2G shows results of stability test of $LacSC_{10}$ hydrogel disks in aqueous media of pH 2, 7.4 and 10 for days 1-21.

Stability of some of the representative hydrogels of the invention in various pH aqueous media was investigated. FIG. 2G shows disks of $LacSC_{10}$ in aqueous media of pH 2, 7.4 and 10 for days 1-21. No observable decrease in disk size or volume confirms hydrogel stability in these media. These hydrogels disks are stable in these aqueous media for over two months, the maximum time investigated.

Microstructure of Hydrogels and Xerogels. One of the most unpredictable and perplexing topics when studying LMW hydrogels is the self-assembly process of hydrogelators which is usually estimated from the microstructure of hydrogels. The microstructure of LMW hydrogels provides information about how the molecules interact with each other and form the network that maintains the hydrogel structure. SEM and TEM are the two most used techniques for investigating hydrogel microstructure through analysis of the corresponding xerogels after flash freezing in liquid nitrogen followed by lyophilization.

Figure 3:
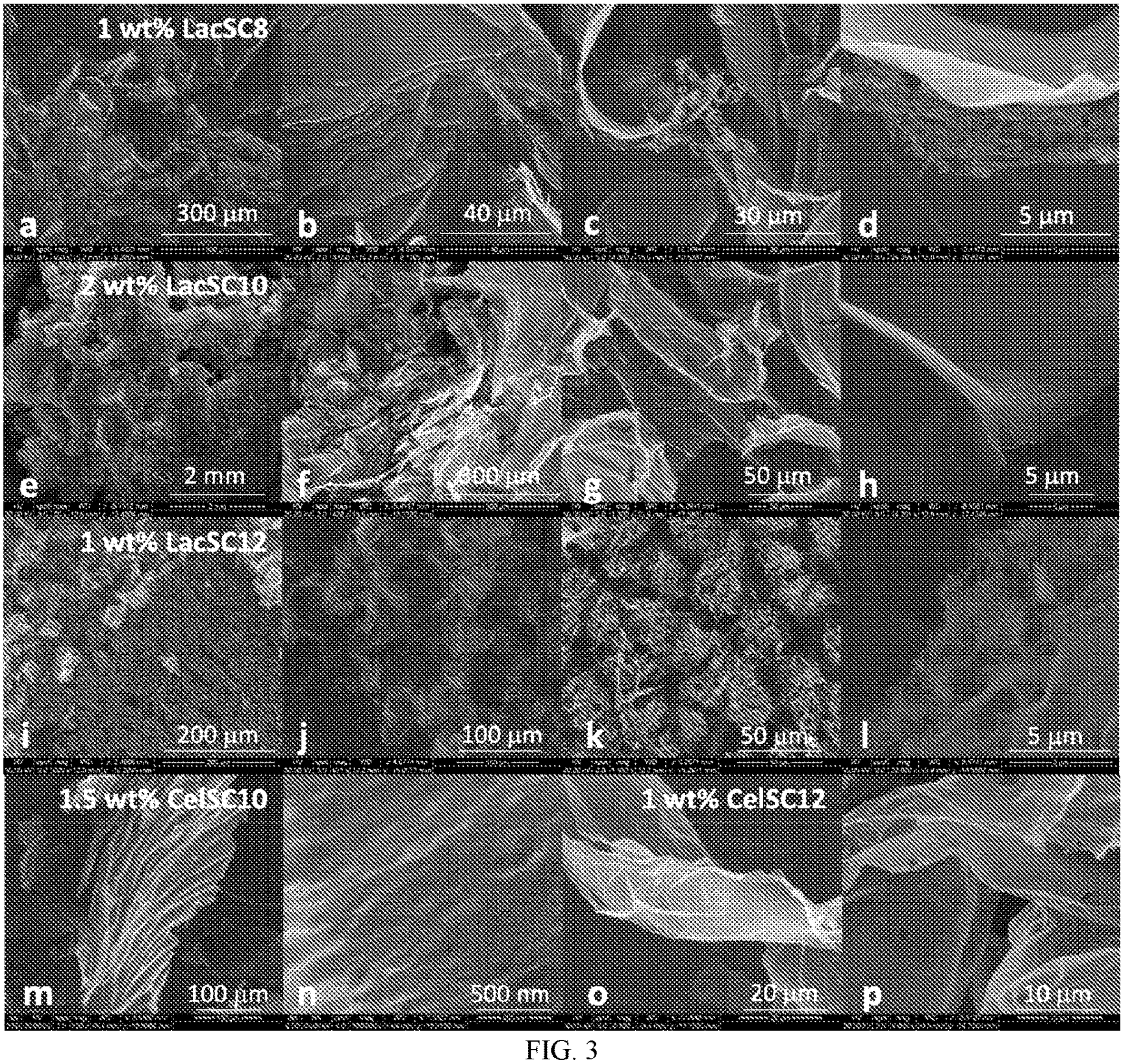
FIG. 3 is representative scanning electron microscopy images of layered xerogels from thioglycolipid hydrogels formed by flash freezing in liquid $N_2$ followed by lyophilization. panels a)-d) show increasing image scale views of 1 wt % $LacSC_8$; panels e)-h) show increasing image scale views of 2 wt % $LacSC_{10}$; panels i)-l) show increasing image scale views of 1 wt % $LacSC_{12}$; panels m) and n) show increasing image scale views of 1.5 wt % $CelSC_{10}$; and panels o) and p) show increasing image scale views of 1 wt % $CelSC_{12}$, respectively.

SEM was performed on xerogel samples to reveal structural details on a 100's of nm to µm scale. Representative images are shown in FIG. 3. The $LacSC_x$ xerogels and those made from the metastable $CelSC_{10/12}$ hydrogels were generally layered structures suggestive of lamellar organization in the hydrogels (FIG. 3 panels a-p) with larger layers formed for the more soluble thioglycolipid systems. The layers can be as large as tens of microns squared for the largest layers observed.

Figure 4:
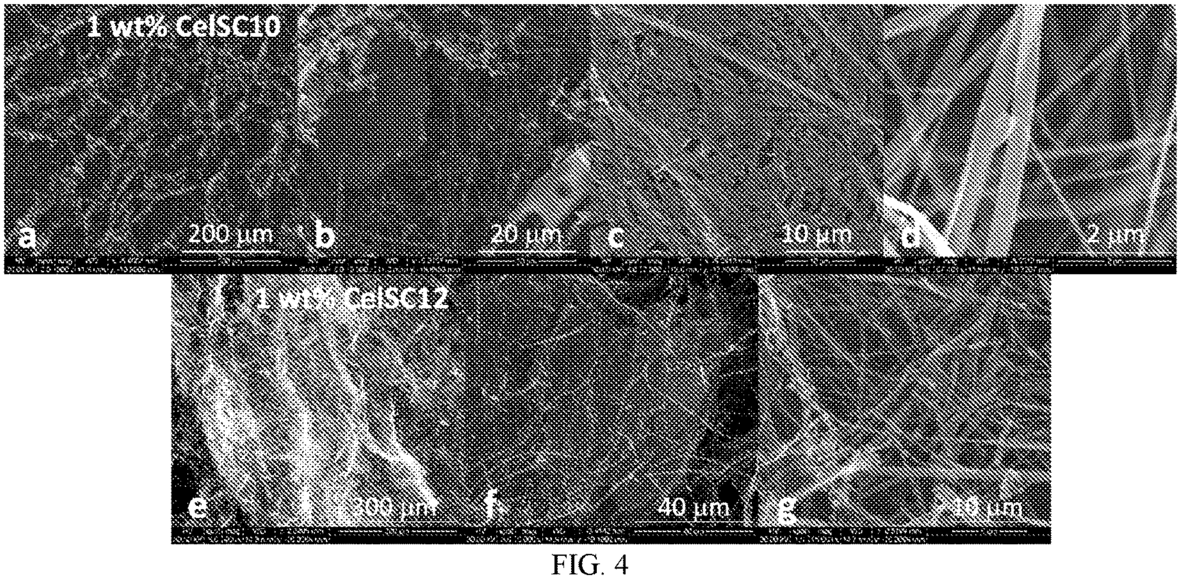
FIG. 4 is representative scanning electron microscopy images of fibrous xerogels from thioglycolipid hydrogels formed by flash freezing in liquid $N_2$ followed by lyophilization. Panels a)-d) show increasing image scale views of 1 wt % $CelSC_{10}$; panels e)-g) show increasing image scale views of 1 wt % $CelSC_{12}$.

Xerogels from the fibrous hydrogels formed by $CelSC_{10}$ and $CelSC_{12}$ were also analyzed. Representative images are shown in FIG. 4. These xerogels were primarily composed of fibrillar crystals, although a small amount of layered structure was sometimes observed. This small amount of residual lamellar structure may be responsible for the overall maintenance of a gel-like state even when the majority of the thioglycolipid has precipitated into matted crystals.

When looking at these hydrogel samples and fibrous samples under SEM, the microstructure can be very diverse given that the gelation process is a competition between molecules aggregating into the hydrogel network and molecules precipitating into other morphologies. The fibrous samples observed clearly represented a situation wherein most of the molecules aggregated into crystals within a small portion of hydrogel network. Similarly, even in hydrogel samples from $LacSC_x$ (x=8,10,12), amorphous aggregates that do not seem to contribute much to the hydrogel network were observed as well. In some cases, for instance, such as for LacSC12 hydrogels, small parts of the surface resembled the fibrous samples from $CelSC_x$ (x=10,12).

Figure 5:
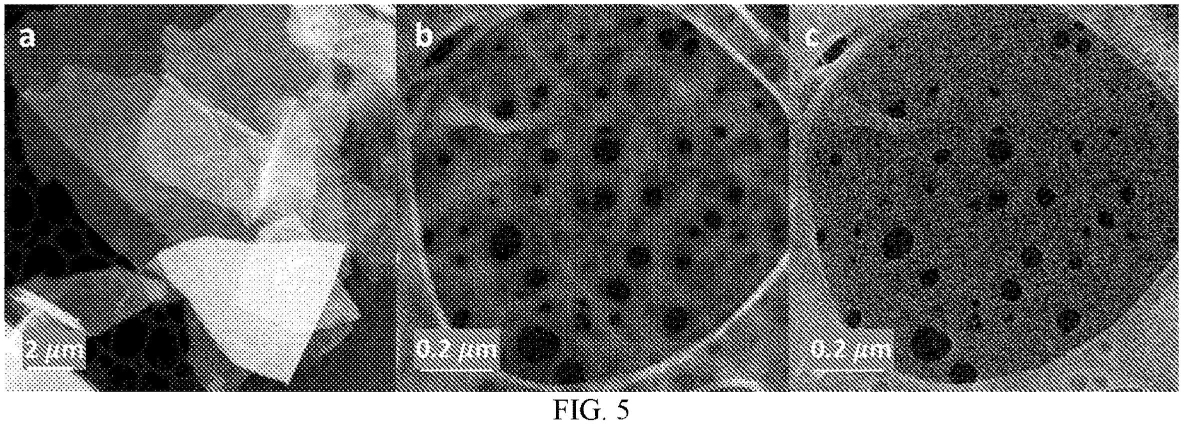
FIG. 5 is representative transmission electron microscopy images of layered xerogels from 1 wt % $LacSC_{10}$ thioglycolipid hydrogels formed by flash freezing in liquid $N_2$ followed by lyophilization with scale bars of 2 μm, 200 nm, and 200 nm in panels a-c, respectively. Images in panels a) and b) were acquired in annular dark field mode whereas image in panel c) was acquired in secondary electron mode.
Figure 6B:
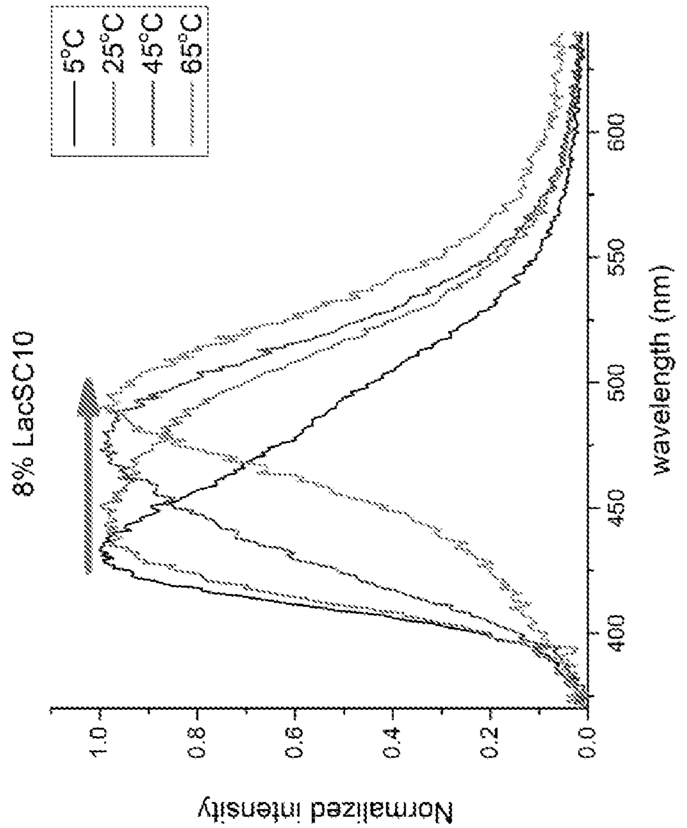
FIG. 6B is representative prodan fluorescence spectra as a function of temperature for 8 wt % $LacSC_{10}$ hydrogel.
Figure 6A:
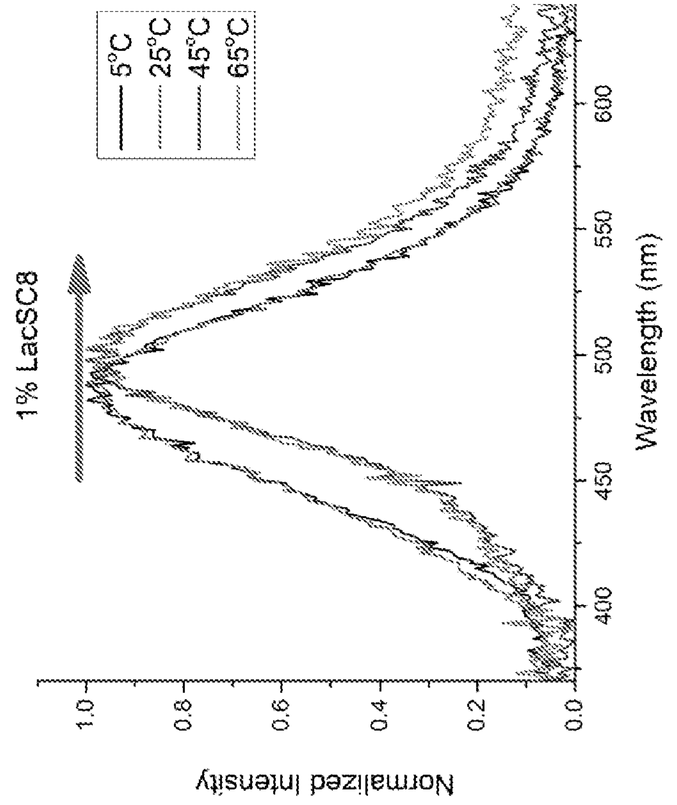
FIG. 6A is representative prodan fluorescence spectra as a function of temperature for 1 wt % $LacSC_8$ hydrogel.
Figure 6C:
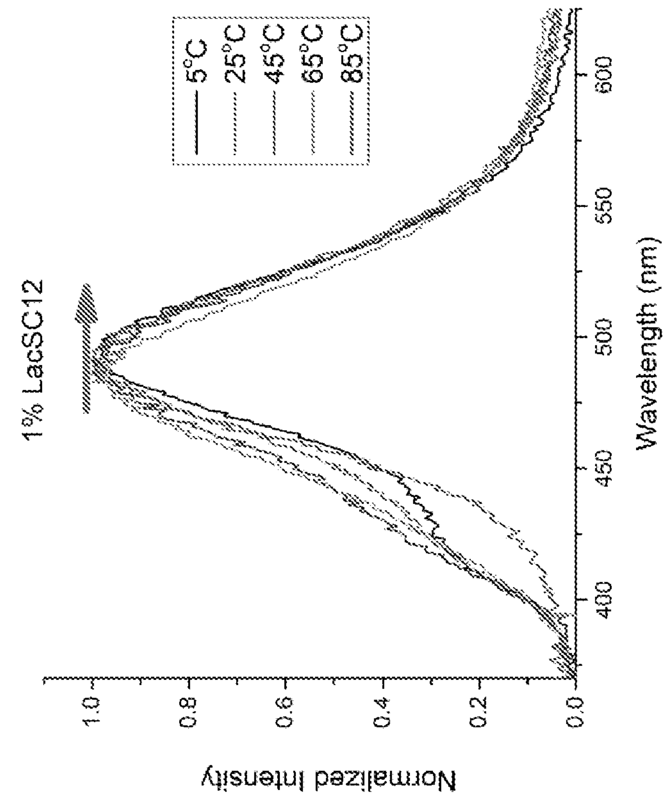
FIG. 6C is representative prodan fluorescence spectra as a function of temperature for 1 wt % $LacSC_{12}$ hydrogel.
Figure 6D:
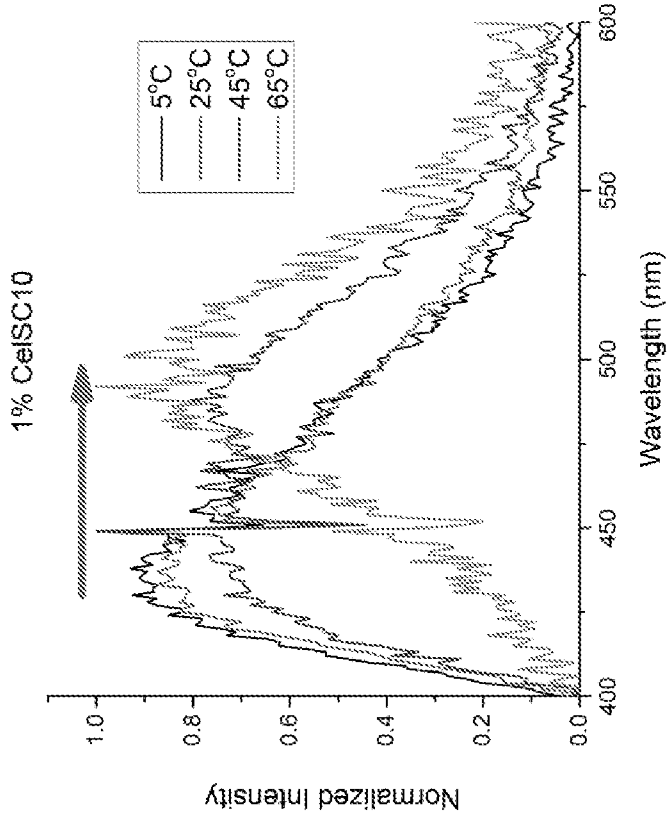
FIG. 6D is representative prodan fluorescence spectra as a function of temperature for 1 wt % $CelSC_{10}$ hydrogel.
Figure 6E:
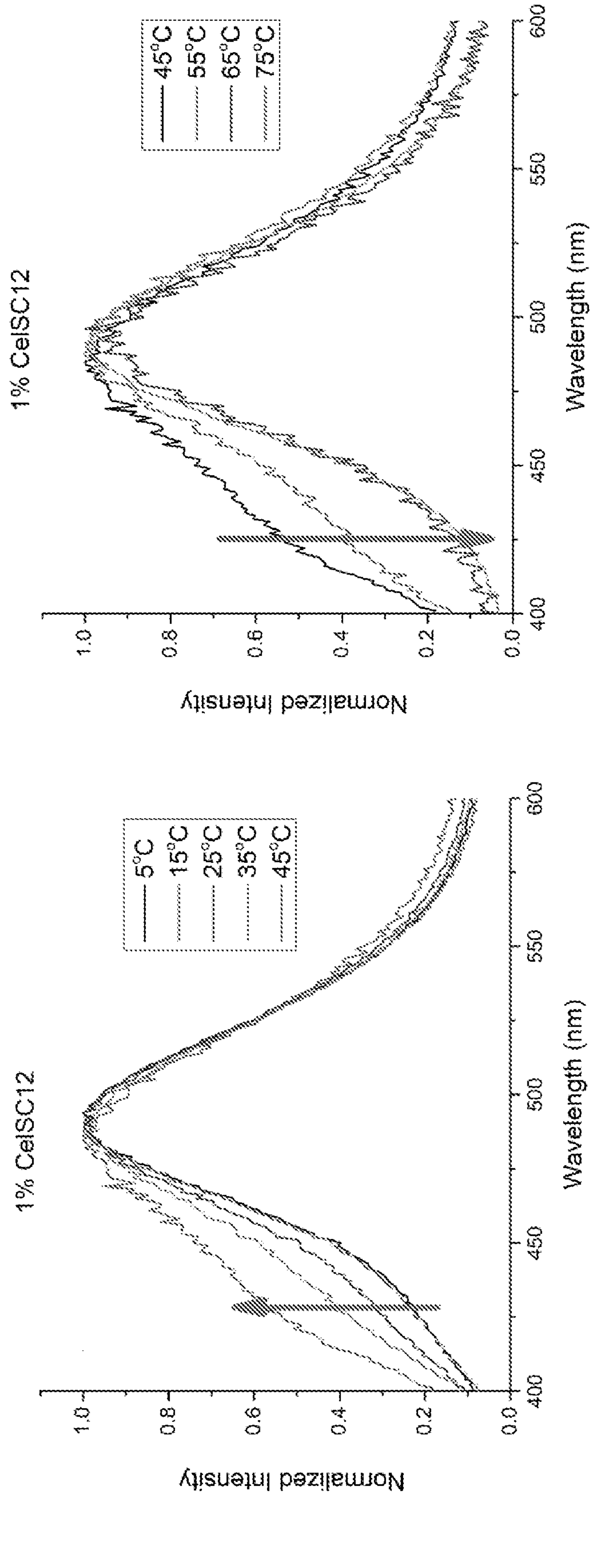
FIG. 6E is representative prodan fluorescence spectra as a function of temperature for 1 wt % $CelSC_{12}$ hydrogel.
Figure 7B:
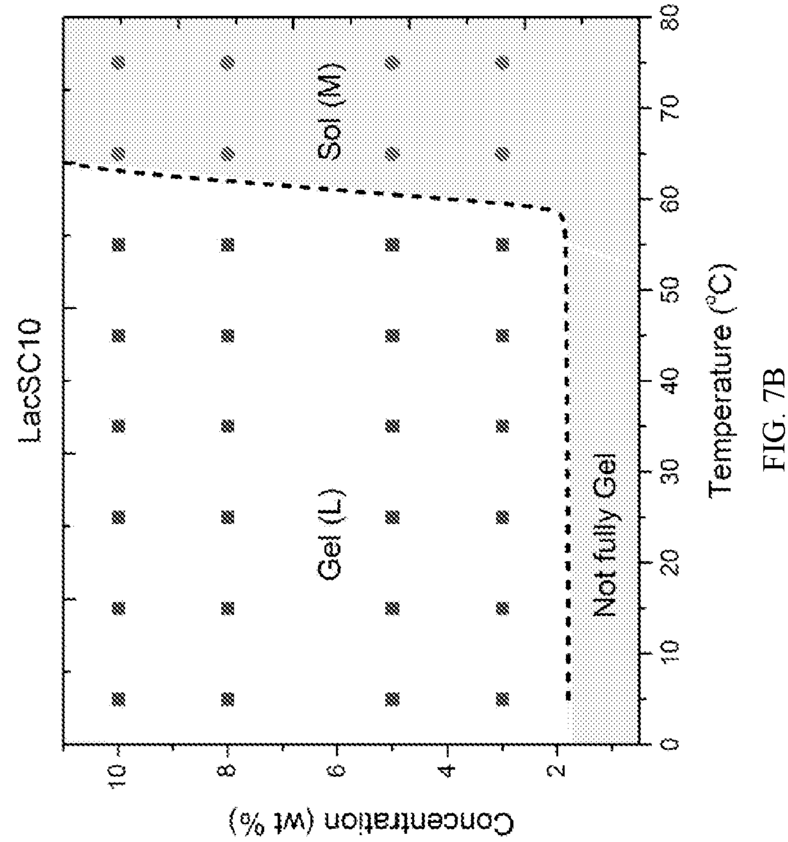
FIG. 7B is the approximate phase diagram for $LacSC_{10}$ hydrogel.
Figure 7A:
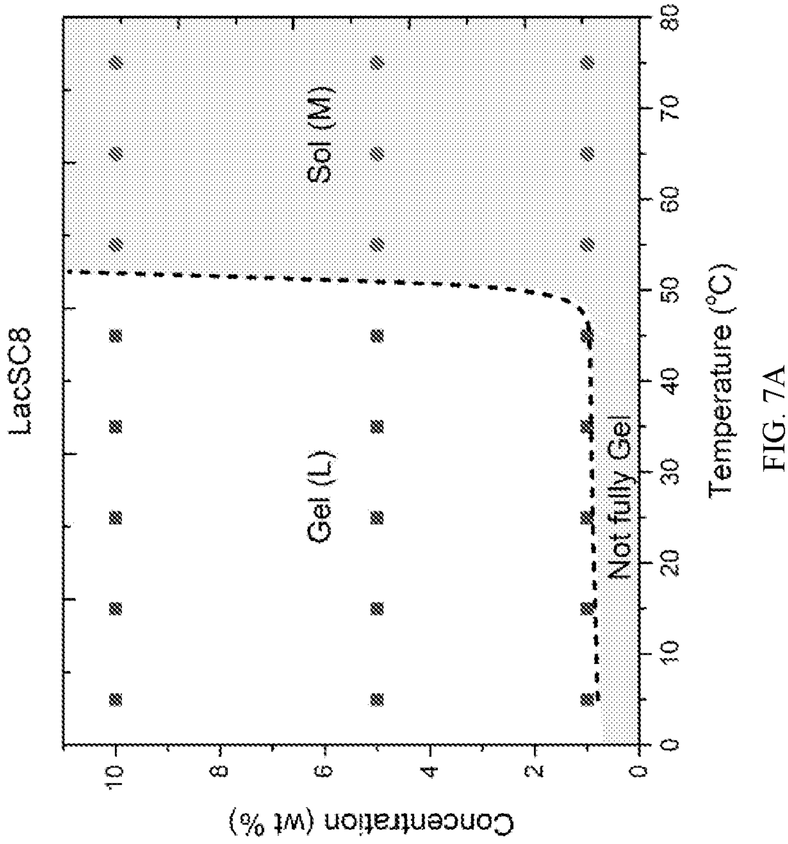
FIG. 7A is the approximate phase diagram for $LacSC_8$ hydrogel deduced from visual assessment, DSC results, rheology, electron microscopy, and prodan fluorescence spectroscopy.
Figure 7D:
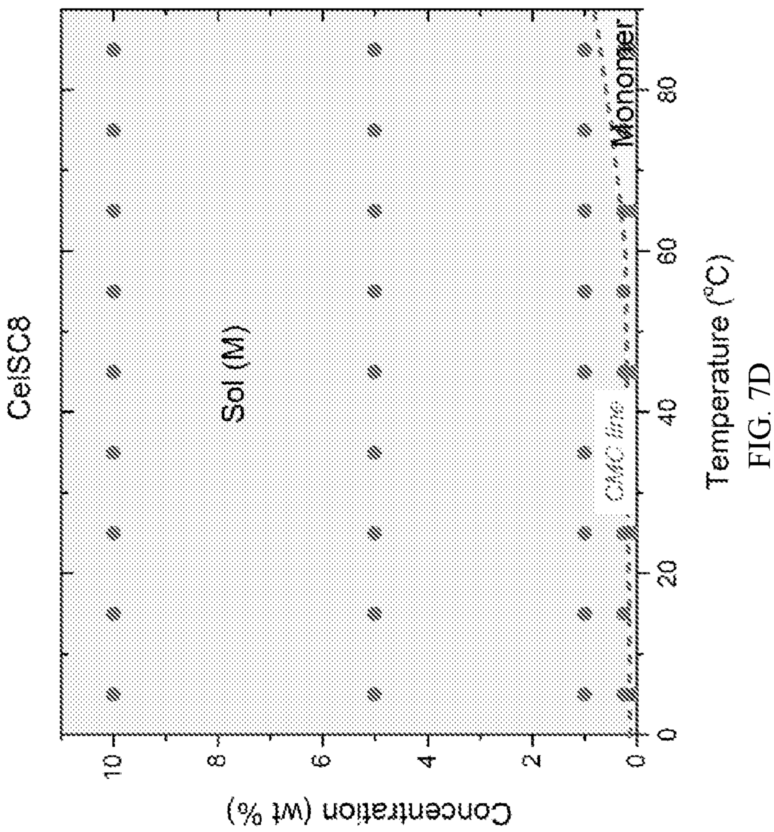
FIG. 7D is the approximate phase diagram for $CelSC_8$ hydrogel.
Figure 7C:
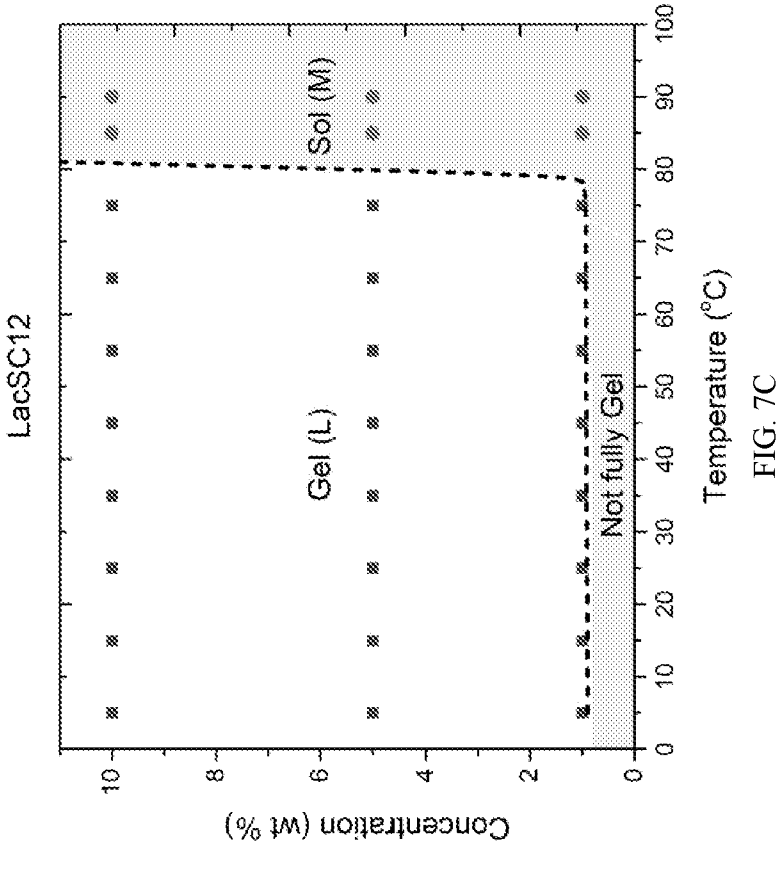
FIG. 7C is the approximate phase diagram for $LacSC_{12}$ hydrogel.
Figure 7F:
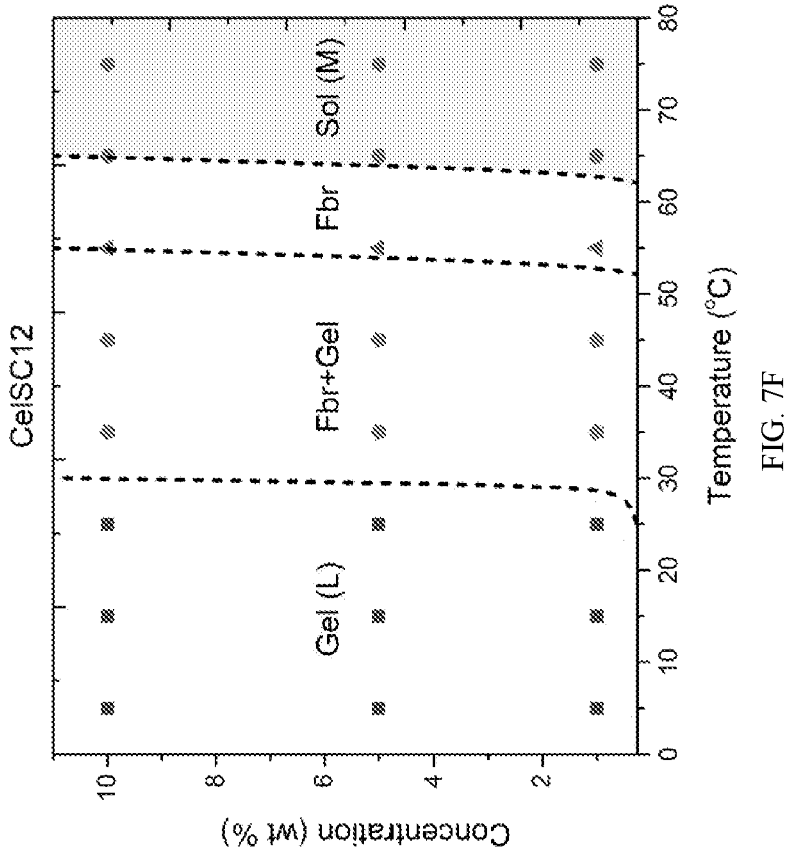
FIG. 7F is the approximate phase diagram for $CelSC_{12}$ hydrogel.
Figure 7E:
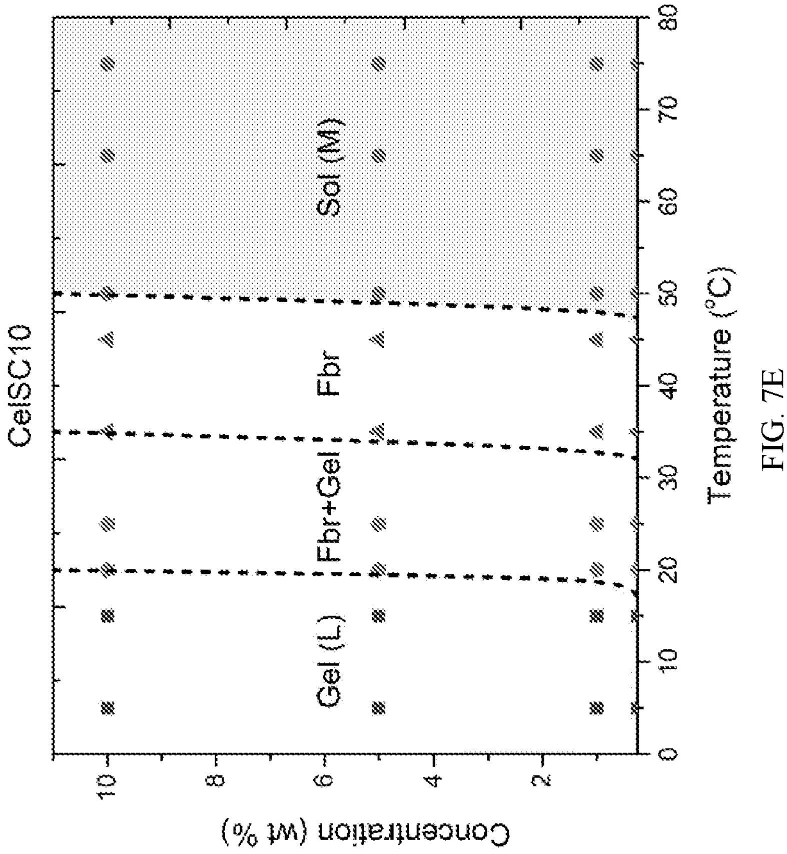
FIG. 7E is the approximate phase diagram for $CelSC_{10}$ hydrogel.

Although the structures of the layered xerogels were revealed by SEM, greater detail on the scale of 10's of nm can be extracted from transmission electron spectroscopy (TEM). TEM analysis was undertaken on the $LacSC_{10}$ hydrogel as a representative system to better understand nanostructure of these xerogels. Representative TEM images are shown in FIG. 5. Panels and b in FIG. 5 were analyzed in the annular dark field mode whereas panel c in FIG. 5 was analyzed in secondary electron mode at the same position as panel b of FIG. 5. The difference between annular dark field mode and secondary electron mode is that the annular dark field mode shows the structural information on both sides of the layers whereas the secondary electron mode shows only the structural features on the top side of the sample.

Panel a in FIG. 5 shows the layered structure on the porous carbon TEM grid at higher resolution. At higher resolution, TEM revealed the presence of random pores in the layered structures that were 20-70 nm in diameter. These pores could be imperfect aggregation of the $LacSC_{10}$ molecules, or they could be generated during the lyophilization process by the rapid extraction of water. More significantly, no obvious aggregation pattern of $LacSC_{10}$ molecules was immediately obvious from these TEM images other than the fact that the molecules are arranged in lamellar structures containing nanoscopic pores. The results obtained from SEM and TEM are intriguing, as the microstructures of most LMW hydrogels reported in the literature are either entangled fibrils or entangled ribbons.

Confirmation of the crystalline nature of the fibrils of $CelSC_{10}$ and $CelSC_{12}$ came from powder and single-crystal x-ray crystallography. Although the molecular packing pattern in single crystals does not necessarily represent the aggregation pattern of molecules in the hydrogel structure, they do provide some possible insight. These results indicate that the molecules are packed in an interdigitated fashion with the cellobiose sugar groups pointing away from the thioalkyl core, consistent with a layered structure.

Aggregation Properties by Fluorescence Spectroscopy. Insight into the structure and microenvironment of these thioglycoside hydrogel systems at different temperatures and concentrations came from fluorescence spectroscopy experiments using the polarity-sensitive fluorophore, prodan. The peak fluorescence emission wavelength for prodan is indicative of the polarity, and hence organization, of its microenvironment, thereby providing insight into the nature of the aggregation occurring. It has been demonstrated previously using aggregation of octyl glucoside that the wavelength of maximum of prodan emission uniquely reports on lyotropic phase state. This emission maximum shifts to shorter wavelengths with increasing order due to a decrease in polarity of the sequestered prodan environment. Free prodan in aqueous solutions had an emission maximum of 525 nm; this emission maximum systematically decreased with increasing organizational order through micellar (M), hexagonal (H), lamellar (L), cubic (C), gel (Gel) and crystalline (Cry) lyotropic phases. For octyl glucoside, the peak emission wavelength for each phase has been reported as follows. These values are expected to shift slightly for different molecular systems, although the order for each phase should remain the same.

| Phase: | Cry | < Gel | < $C$ | << $L$ | < $H$ | < $M$ | < $H_2O$ |
|---|---|---|---|---|---|---|---|
| $\lambda_{max}$(nm): | 380 | 400 | 410 | 473 | 485 | 490 | 525 |

For these thioglycolipid hydrogels, the change in organization and phase with concentration and temperature are portrayed by the representative prodan fluorescence behavior shown in FIGS. 6A-6E for five thioglycolipid hydrogels. These fluorescence spectra represent a composite of prodan dye responses from the dye both imbedded in the hydrogel microstructure (typically <10 wt %) as well as the prodan in micelles aggregates that coexist with this hydrogel microstructure in the predominant water portion (typically >90 wt %) of these hydrogels. These emission spectra demonstrated that heating the gels above their gel-sol transition temperatures results in prodan fluorescence with an emission $\lambda_{max}$ at 494-500 nm indicative of a purely micellar system as the hydrogel microstructure of the thioglycolipids dissolves. Based on the lamellar structures substantiated by the SEM and TEM results, the emission band with a $\lambda_{max}$ of 487-490 nm that dominated the spectra from all thioglycolipids in the hydrogel state at temperatures below the gel-sol transition temperature was assigned to the aqueous micellar phase state. An additional band is observed at an emission $\lambda_{max}$ at 423-438 nm due to prodan in the minor component lamellar microstructure of these hydrogel. This band was only observed from hydrogels from higher concentration solutions of $LacSC_8$ but all concentrations of $LacSC_{10}$, $LacSC_{12}$, $CelSC_{10}$, and $CelSC_{12}$ studied here, including those metastable lamellar gels from $CelSC_{10}$ and $CelSC_{12}$ that had converted to crystalline fibrous structures. This band is presumed to result from prodan molecules fully embedded into the very hydrophobic chain regions of these lamellar or fibrous thioglycolipid hydrogels.

Combining the results obtained from prodan fluorescence, differential scanning calorimetry, visual assessment, and rheology, approximate phase diagrams were constructed for each thioglycolipid system studied. These are shown in FIGS. 7A-7F.

Typical phase diagrams of amphiphilic molecules include mainly three regions: solid, monomers and micelles. The solid region usually lies in the low temperature and high concentration regime. This regime represents the concentration and temperature range wherein the amphiphile is not soluble in the solvent. The monomer region usually lies in the low concentration regime across all temperatures. In this range of concentration and temperature, the amphiphilic molecules are soluble in the solvent but not at a concentration high enough to drive aggregation and formation of micelles. The third regime, wherein the concentration is above the critical micelle concentration (CMC), is the regime wherein the concentration and temperature are sufficient to support aggregation and the formation of different lyotropic phases. The phase diagrams depicted in FIGS. 7A-7F for the thioglycolipid hydrogels can be understood within this framework. The hydrogel network can be designated as the solid phase wherein the thioglycolipids either aggregate into extensive lyotropic organized assemblies to remove themselves from solution or formally crystallize to precipitate out of solution. As such, the hydrogel (solid) regime must lie in the low temperature range and cannot exist at low concentration. Moreover, as temperature increases, the hydrogel (solid) phase will cross into the micelle regime, which represents "melting" of the hydrogel into a less well organized solution state. This gel-sol transition is where the temperature exceeds the solubility line and the thioglycolipids form either monomers or micelles. Because the concentrations studied are considerably above the CMC values for these systems, the lyotropic phase was only observed in the prodan fluorescence experiments. For thiocellobiosides, two states are possible below the solubility line, the gel and fiber states, both of which result from limits in solubility in aqueous solution.

Figure 8A:
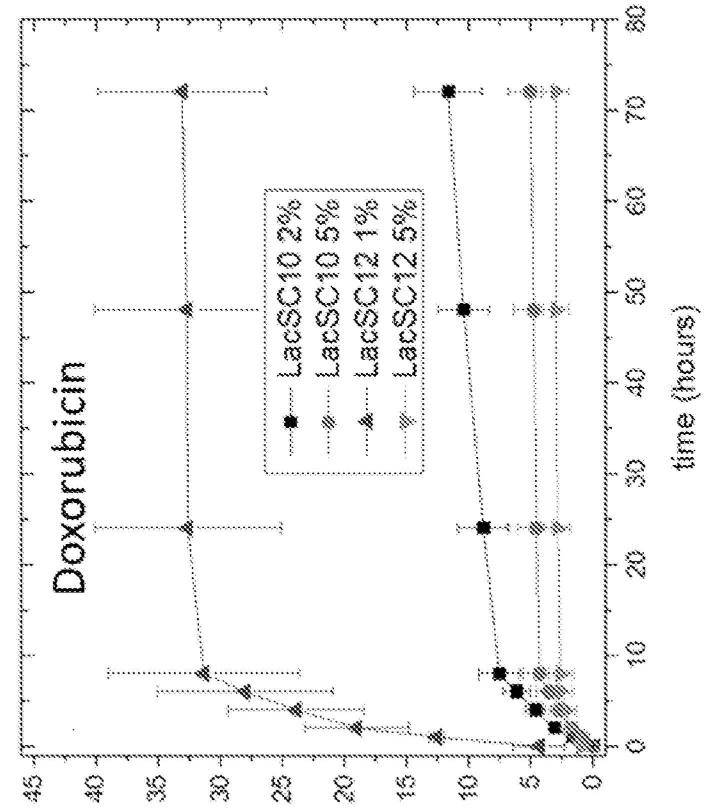
FIG. 8A is time dependent release profiles for a representative hydrophobic molecular cargo, doxorubicin determined using fluorescence spectroscopy.
Figure 8B:
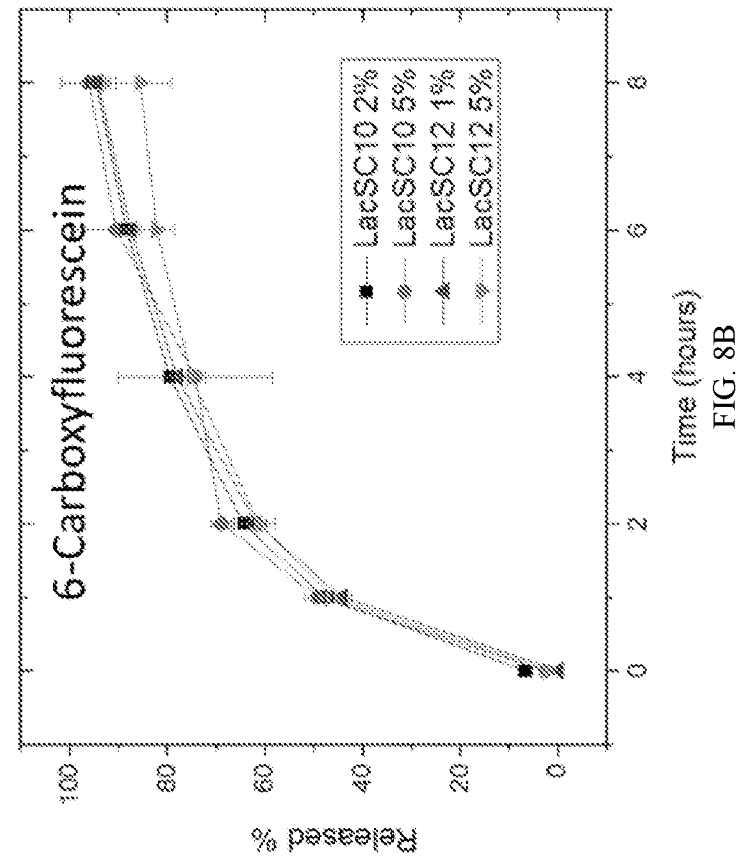
FIG. 8B is time dependent release profiles for a representative hydrophilic molecular cargo, 6-carboxyfluorescein determined using fluorescence spectroscopy.

Hydrogel Cargo Release Characteristics. Release profiles for these hydrogels for two major classes of molecular cargo, hydrophobic and hydrophilic, were characterized using fluorescence spectroscopy. Such release properties are of interest for therapeutic agent delivery or agrochemical delivery applications of the invention. Doxorubicin was chosen as a representative example of hydrophobic molecular cargo and 6-carboxyfluorescein (6-FAM) was chosen as a representative example of hydrophilic molecular cargo. In these studies, the hydrogels were loaded with the cargo species during hydrogelation and the resulting loaded gels were then submerged in aqueous solutions for varying amounts of time. The aqueous media above the hydrogel was periodically exchanged for fresh media and the medium removed was analyzed for the presence of molecular cargo species using fluorescence spectroscopy. Release profiles for these cargo compounds are shown in FIGS. 8A and 8B.

The release profiles demonstrated the delivery of some level of both hydrophobic and hydrophilic cargo into solution around the hydrogel. In general, a hydrophilic cargo is released more completely and more rapidly than hydrophobic cargo.

Figure 8C:
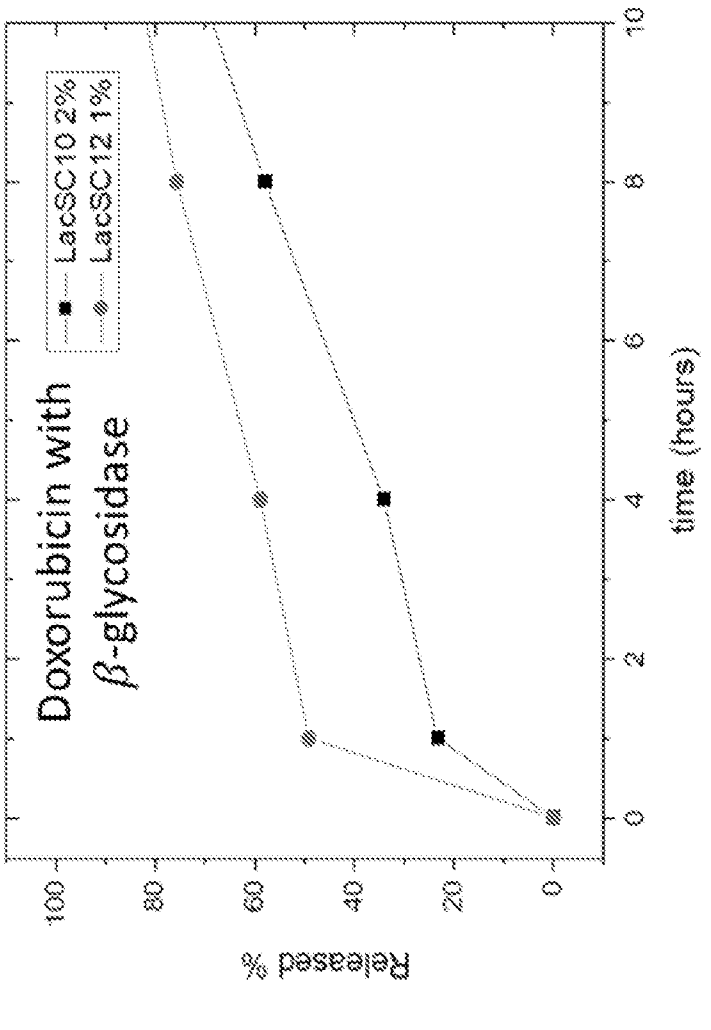
FIG. 8C is time dependent release profiles for doxorubicin in the presence of a small amount of β-glycosidase determined using fluorescence spectroscopy.

In physiological milieu such as might be experienced in therapeutic agent delivery, or environmental soil or water milieu such as might be experienced in agrochemical delivery, there is the additional possibility of enzymatically-assisted or microbially-assisted release of molecular cargo through partial degradation of the hydrogel. This possibility was tested using β-glycosidase as an enzyme contained in the aqueous medium surrounding the hydrogel loaded with molecular cargo. The results shown in FIG. 8C confirm enzymatically-assisted cargo delivery from these hydrogels.

LMW hydrogels have attracted considerable interest with many attempts to utilize sugar-based LMW hydrogelators for various applications. The present invention provides novel disaccharide-based thioglycolipids through green synthetic processes along with characterization of the hydrogel physical properties.

The present inventors have discovered a new analogue of sugar-based LMWGs that possess high G' values with intriguing microstructures, and surprising and unexpected properties and behaviors. The linear β (1→4) linkage in the lactose and cellobioside headgroups impose unique structural effects to the assembly process. Not only do the distinguished properties of these materials attribute a new analogue of LMW hydrogels for potential applications, but also the design of molecular structure that leads to these unique properties provide deeper insight in self-assembly and molecular packing of glycosylated-amphiphiles as potential low molecular weight hydrogelators.

Hydrogel Microparticles by Droplet Microfluidics. Particles in the size range of 40-60 μm diameter were fabricated using droplet microfluidics. LacSC8 hydrogel particles were formed using a 1 wt % aqueous LacSC8 solution as the droplet phase delivered at 10 μL/min into the droplet forming junction of a droplet microfluidic device held at 45 °C with toluene, dibutyl phthalate (DBP) or a mixture of toluene+DBP as the carrier phase at 20.8 μL/min. Droplets were collected in a chilled vessel containing either water, toluene or DBP. Particles of CelSC10 were similarly formed in an identical microfluidic device at 45 °C using an aqueous 1 wt % droplet solution of CelSC10 at 10 μL/min with a carrier phase of DBP at 20.8 μL/min. Droplets were collected in a chilled vessel containing either water, toluene or DBP. After collection, these particles were stable in solution at room temperature for over 1 week (the maximum time studied).

Figure 9:
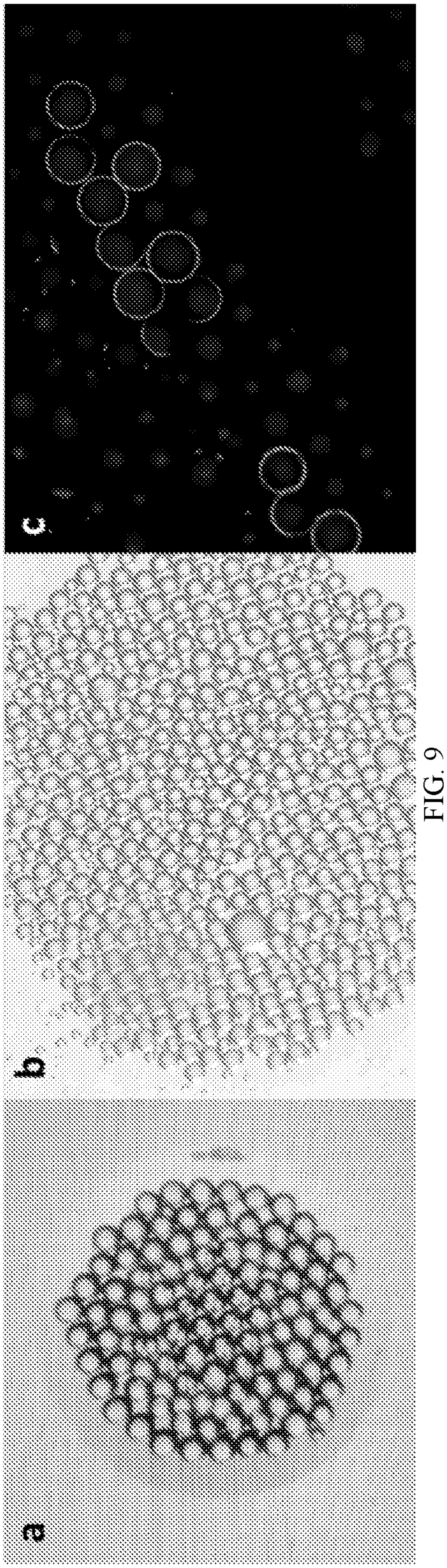
FIG. 9 shows a bright field microscopy image of representative microparticle hydrogels of the invention. In particular, panel a shows a bright field microscopy image of microparticles of CelSC10 hydrogel; panel b shows a bright field microscopy image of LacSC8 hydrogel particles; and panel c shows a fluorescence microscopy image of LacSC8 microparticles stained with Texas Red.

Bright field microscopy and fluorescence microscopy with Texas Red staining were used to characterize the resulting hydrogel microparticles. See FIG. 9. In particular, panel a of FIG. 9 shows a bright field microscopy image of microparticles of $CelSC_{10}$ hydrogel; panel b of FIG. 9 shows a bright field microscopy image of $LacSC_8$ hydrogel particles; and panel c of FIG. 9 shows a fluorescence microscopy image of $LacSC_8$ microparticles stained with Texas Red.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:

1. A biocompatible low molecular weight ("LMW") hydrogel having a high storage modulus, wherein said LMW hydrogel comprises at least 80% water and thioglycolipid that are non-cross linked.

2. The biocompatible low molecular weight non-cross-linked hydrogel of claim 1, wherein said hydrogel is non-fibrous 3-D network.

3. The biocompatible low molecular weight non-cross-linked hydrogel of claim 1, wherein at least 90% of said LMW hydrogel is water.

4. The biocompatible low molecular weight non-cross-linked hydrogel of claim 1, wherein the amount of thioglycolipid in said LMW hydrogel ranges from about 0.5% to about 20% by weight.

5. The biocompatible low molecular weight non-cross-linked hydrogel of claim 1, wherein the storage modulus of said LMW hydrogel is at least about 10 kPa at 25 °C.

6. The biocompatible low molecular weight non-cross-linked hydrogel of claim 1, wherein said thioglycolipid comprises a disaccharide that is linked to a lipid via a thiol linkage.

7. The biocompatible low molecular weight non-cross-linked hydrogel of claim 1, wherein said thioglycolipid is of the formula: A-B, wherein:

A is a 1→4 linked disaccharide sugar moiety that is linked to B through a thioether linkage, and B is $C_8$-$C_{20}$ alkyl.

8. A carrier material comprising (a) a LMW hydrogel of claim 1 and (b) a cargo.

9. The carrier material of claim 8, wherein said cargo is a therapeutic agent or prophylactic agent.

10. The carrier material of claim 8, wherein said cargo is an absorbing material, a substrate in tissue engineering or cell culture.

11. An article of manufacture comprising a LMW hydrogel of claim 1.

12. The article of manufacture according to claim 11, wherein said article of manufacture comprises a wound healing material, tissue engineering or repair material, cell culture material, or controlled-release drug delivery material.

13. The article of manufacture according to claim 11, wherein said article of manufacture comprises microparticles or nanoparticles of the LMW hydrogel, and wherein the microparticles or nanoparticles of LMW hydrogel comprises a cargo.

14. The article of manufacture according to claim 13, wherein said cargo is a therapeutic agent, a prophylactic agent, an indicator moiety, a labelling moiety, an environmental tracer, a complex-forming agent that forms a complex with a heavy metal or a rare earth element, or an agrochemical.

15. The article of manufacture according to claim 13, wherein said cargo comprises a rhamnolipid, a mono- or disaccharide analogue, or a combination thereof.

16. An article of manufacture comprising a microparticle or a nanoparticle, wherein said microparticle or a nanoparticle comprises a core and a shell, and wherein said core comprises a magnetic material and said shell comprises the LMW hydrogel of claim 1 and a cargo.

17. The article of manufacture according to claim 16, wherein said core comprises iron, nickel, cobalt, or a combination thereof.

18. A low molecular weight physical hydrogel comprising at least about 80% by weight of water and from about 0.5% to 20% by weight of thioglycolipid having a storage modulus of at least about 10 kPa at 25 °C.

19. The low molecular weight physical hydrogel of claim 18, wherein said thioglycolipid is of the formula: A-B, wherein:

A is a 1→4 linked disaccharide sugar moiety that is linked to B through a thioether linkage, and B is $C_8$-$C_{20}$ alkyl.

20. The low molecular weight physical hydrogel of claim 18 having a storage modulus (G') ranging from about 10 kPa to about 570 kPa.

* * * * *